United States Patent [19]

Fujii, deceased et al.

[11] Patent Number: 5,145,865
[45] Date of Patent: Sep. 8, 1992

[54] PHENYLCARBOXYLIC ACID DERIVATIVES HAVING HETERO RING

[75] Inventors: Setsuro Fujii, deceased, late of Kyoto, Japan, by Keiko Fujii, administrator; by Shinichiro Fujii, administrator, Uji, Japan; by Kaoruko Takada, administrator, Ehime, Japan; Hiroyuki Kawamura; Shinichi Watanabe, both of Otsu, Japan

[73] Assignee: Otsuka Pharmaceutical Company, Limited, Tokyo, Japan

[21] Appl. No.: 511,344

[22] Filed: Apr. 19, 1990

[30] Foreign Application Priority Data

Apr. 19, 1989 [JP] Japan ................... 1-10439
Feb. 9, 1990 [JP] Japan ................... 2-30839

[51] Int. Cl.$^5$ ............ C07D 207/26; C07D 211/10; A61K 31/40; A61K 31/445
[52] U.S. Cl. .............. 514/424; 548/550; 548/551; 546/243; 546/248; 514/317; 514/345
[58] Field of Search ......... 548/551, 550; 514/424, 514/317, 345; 546/243, 248

[56] References Cited

U.S. PATENT DOCUMENTS

| | | | |
|---|---|---|---|
| 4,073,935 | 2/1978 | Grill et al. | 424/308 |
| 4,109,013 | 8/1978 | Grill et al. | 424/308 |
| 4,144,351 | 3/1979 | Grill et al. | 424/308 |
| 4,831,055 | 5/1989 | Yoshikumi et al. | 514/539 |

FOREIGN PATENT DOCUMENTS 1516747 7/1978 United Kingdom .

*Primary Examiner*—David B. Springer
*Attorney, Agent, or Firm*—Wegner, Cantor, Mueller & Player

[57] ABSTRACT

Phenylcarboxylic acid derivatives having a hetero ring in the substituent of the formula:

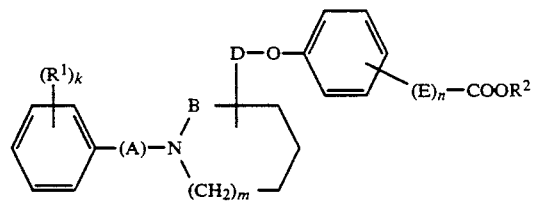

wherein $R^1$ is halogen, alkyl, cycloalkyl, hydroxy, alkoxy, phenoxy which has a substituent selected from halogen and alkyl, carboxyl, alkylsulfonyloxy, phenylsulfonyloxy optionally substituted by halogen, alkylsulfonyloxyalkoxy, amino, alkanoylamino, benzoylamino, alkenyloxy, phenylalkoxyalkoxy, hydroxyalkoxy, phenylalkoxy having optionally 1 to 3 substituents selected from halogen, alkyl and alkoxy, halogenoalkyl, cycloalkyloxy optionally substituted by hydroxy, alkoxy substituted by cycloalkyl having optionally hydroxy substituent, imidazolylalkyl or imidazolylalkoxy; k is 0 or 1 to 3; or $(R^1)_k$ is alkylenedioxy; A is alkylene or alkylenoxy; l is 0 or 1; B is methylene or carbonyl; m is 0 or 1; D is alkylene; E is alkylene or alkenylene; n is 0 or 1; and $R^2$ is hydrogen or alkyl, or a salt thereof, which have fatty acid synthesis-inhibitory activity, cholesterol synthesis-inhibitory activity and are useful as antilipidemic agent, prophylactic and treating agent of arteriosclerosis, prophylactic and treating agent of obesity, antidiabetics.

24 Claims, No Drawings

PHENYLCARBOXYLIC ACID DERIVATIVES HAVING HETERO RING

TECHNICAL FIELD

This invention relates to novel phenylcarboxylic acid derivatives having a hetero ring in the substituent, and salts thereof, more particularly, to compounds having hypolipidemic activity and being useful as a medicament.

TECHNICAL BACKGROUND

There have been known some compounds having hypolipidemic activity, for example, 1,3-disubstituted propanol derivatives disclosed in U.S. Pat. Nos. 4,073,935, 4,109,013 and 4,144,351, and British Patent 1,516,747, but this invention provides novel phenylcarboxylic acid derivatives and salts thereof which have a different structure from these known compounds and are particularly useful as a medicament.

DISCLOSURE OF THE INVENTION

This invention provides phenylcarboxylic acid derivatives having a hetero ring in the substituent and salts thereof, which have the following formula:

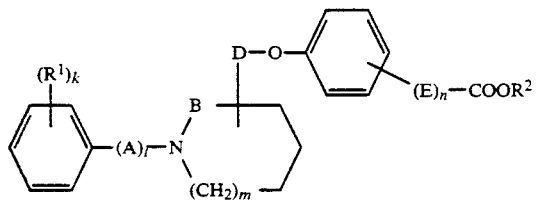

(1)

wherein
$R^1$ is a halogen atom, a lower alkyl group, a cycloalkyl group, a hydroxy group, a lower alkoxy group, a phenoxy group which has a substituent selected from a halogen atom and a lower alkyl group, a carboxyl group, a lower alkylsulfonyloxy group, a phenylsulfonyloxy group which may optionally be substituted by a halogen atom, a lower alkylsulfonyloxy(lower)alkoxy group, an amino group, a lower alkanoylamino group, a benzoylamino group, a lower alkenyloxy group, a phenyl(lower)alkoxy(lower)alkoxy group, a hydroxy-substituted lower alkoxy group, a phenyl(lower)alkoxy group which may optionally have one to three substituents selected from a halogen atom, a lower alkyl group and a lower alkoxy group on the phenyl ring, a halogen-substituted lower alkyl group, a $C_3$–$C_8$ cycloalkyloxy group which may optionally be substituted by a hydroxy group, a lower alkoxy group substituted by a $C_3$–$C_8$ cycloalkyl group having optionally a hydroxy substituent, an imidazolyl(lower)alkyl group, or an imidazolyl(lower)alkoxy group; k is 0 or an integer of 1 to 3; or $(R^1)_k$ may be a lower alkylenedioxy group;
A is a lower alkylene group or a lower alkylenoxy group;
l is 0 or 1;
B is a methylene group or a carbonyl group;
m is 0 or 1;
D is a lower alkylene group;
E is a lower alkylene group or a lower alkenylene group;
n is 0 or 1; and
$R^2$ is a hydrogen atom or a lower alkyl group, or a salt thereof.

In the present specification, when k is in the group: $(R^1)_k$ is 2 or 3, each $R^1$ may be the same as or different from each other in the groups as defined above.

It is assumed that when the compounds of the formula (1) and their salts of this invention are administered, they are esterified with CoA in the living body and inhibit strongly cholesterol- and fatty acids-biosynthetic enzymes and thereby exhibit activity of inhibiting fatty acids-synthesis and activity of inhibiting cholesterol-synthesis. Further, they are well absorbed into the living body and have durable pharmacological activity, higher safety, excellent absorbability and discharging property and also low toxicity. Accordingly, these compounds are useful as a medicament such as hypolipidemic drug, prophylactic and treating agent of artereosclerosis, prophylactic and treating agent of obesity, antidiabetics, and the like.

The groups as defined for A, B, D, E, $R^1$ and $R^2$ and others in the present specification include specifically the following groups.

The halogen atom includes fluorine, chlorine, bromine and iodine.

The lower alkyl group includes straight chain or branched chain alkyl groups having 1 to 6 carbon atoms, such as methyl, ethyl, propyl, isopropyl, butyl, isobutyl, tertbutyl, pentyl, hexyl, and the like.

The cycloalkyl group includes cycloalkyl groups having 3 to 8 carbon atoms, such as cyclopropyl, cyclobutyl, cyclopentyl, cyclohexyl, cycloheptyl, cyclooctyl, and the like.

The lower alkoxy group includes straight chain or branched chain alkoxy groups having 1 to 6 carbon atoms, such as methoxy, ethoxy, propoxy, isopropoxy, butoxy, tertbutoxy, pentyloxy, hexyloxy, and the like.

The phenoxy group which has a substituent selected from a halogen atom and a lower alkyl group includes phenoxy, phenoxy groups having a halogen substituent on the phenyl ring such as 2-chlorophenoxy, 3-chlorophenoxy, 4-chlorophenoxy, 2-fluorophenoxy, 3-fluorophenoxy, 4-fluorophenoxy, 2-bromophenoxy, 3-bromophenoxy, 4-bromophenoxy, 2-iodophenoxy, 3-iodophenoxy, 4-iodophenoxy, and the like, and phenoxy groups having a substituent of an alkyl group having 1 to 6 carbon atoms on the phenyl ring such as 2-methylphenoxy, 3-methylphenoxy, 4-methylphenoxy, 2-ethylphenoxy, 3-propylphenoxy, 4-isopropylphenoxy, 4-tert-butylphenoxy, 2-pentylphenoxy, 3-hexylphenoxy, 4-hexylphenoxy, and the like.

The lower alkylsulfonyloxy group includes sulfonyloxy groups substituted by the above-mentioned lower alkyl groups.

The phenylsulfonyloxy group which may optionally be substituted by a halogen atom includes phenylsulfonyloxy groups which may optionally have one to three substituents of a halogen atom.

The lower alkylsulfonyloxy(lower)alkoxy group includes lower alkoxy groups substituted by the above-mentioned lower alkylsulfonyloxy groups.

The lower alkanoylamino group includes amino groups substituted by alkanoyl groups having 2 to 6 carbon atoms, such as acetylamino, propionylamino, butyrylamino, pentanoylamino, hexanoylamino, and the like.

The lower alkenyloxy group includes alkenyloxy groups having 2 to 6 carbon atoms, such as vinyloxy, allyloxy, 1-propenyloxy, butenyloxy, pentenyloxy, hexenyloxy, and the like.

The phenyl(lower)alkoxy(lower)alkoxy group includes lower alkoxy groups substituted by phenyl(lower)alkoxy groups wherein the alkoxy moiety has straight chain or branched chain and has 1 to 6 carbon atoms, such as phenylmethoxymethoxy, 1-phenylmethoxyethoxy, 2-phenylmethoxypropoxy, 4-phenylmethoxybutoxy, 5-phenylmethoxypentyloxy, 6-phenylmethoxyhexyloxy, 1-phenylethoxymethoxy, 1-phenylethoxyethoxy, 2-phenylethoxypropoxy, and the like.

The hydroxy-substituted lower alkoxy group includes straight chain or branched chain alkoxy groups having 1 to 6 carbon atoms which are substituted by one to three hydroxy groups, such as hydroxymethoxy, 2-hydroxyethoxy, 2-hydroxypropoxy, 2-hydroxyisopropoxy, 4-hydroxybutoxy, 2-hydroxytert-butoxy, 5-hydroxypentyloxy, 6-hydroxyhexyloxy, 1,2-dihydroxypropoxy, 1,2,3-trihydroxybutoxy, 1,1,4-trihydroxybutoxy, and the like.

The phenyl(lower)alkoxy group which may optionally have one to three substituents selected from a halogen atom, a lower alkyl group and a lower alkoxy group on the phenyl ring includes unsubstituted phenylalkoxy groups wherein the alkoxy moiety is a straight chain or branched chain alkoxy group having 1 to 6 carbon atoms such as benzyloxy, 2-phenylethoxy, 3-phenylpropoxy, 4-phenylbutoxy, 1,1-dimethyl-2-phenylbutoxy, 5-phenylpentyloxy, 6-phenylhexyloxy, and the like; and phenylalkoxy groups wherein the alkoxy moiety is a straight chain or branched chain alkoxy group having 1 to 6 carbon atoms, which have one to three substituents selected from a halogen atom, a straight chain or branched chain alkyl group having 1 to 6 carbon atoms and a straight chain or branched chain alkoxy group having 1 to 6 carbon atoms on the phenyl ring, such as 2-chlorobenzyloxy, 3-chlorobenzyloxy, 4-chlorobenzyloxy, 2-bromobenzyloxy, 3-bromobenzyloxy, 4-bromobenzyloxy, 2-fluorobenzyloxy, 3-fluorobenzyloxy, 4-fluorobenzyloxy, 2iodobenzyloxy, 3-iodobenzyloxy, 4-iodobenzyloxy, 2-methylbenzyloxy, 3-methylbenzyloxy, 4-methylbenzyloxy, 2-ethylbenzyloxy, 3-propylbenzyloxy, 4-methylbenzyloxy, 4-tert-butylbenzyloxy, 2-pentylbenzyloxy, 3-hexylbenzyloxy, 2-(2-chlorophenyl)ethoxy, 3-(4-bromophenyl)propoxy, 1,1-dimethyl-2-(3-fluorophenyl)butoxy, 6-(4-chlorophenyl)hexyloxy, 2-(4-ethylphenyl)ethoxy, 3-(2-methylphenyl)propoxy, 2-(4-tert-butylphenyl)hexyloxy, 6-(4-tert-butylphenyl)hexyloxy, 6-(4-hexylphenyl)hexyloxy, 4-methoxybenzyloxy, 2-ethoxybenzyloxy, 3-propyloxybenzyloxy, 4-isopropyloxybenzyloxy, 4-tert-butyloxybenzyloxy, 2-pentyloxybenzyloxy, 3-hexyloxybenzyloxy, 2-(2-methoxyphenyl)ethoxy, 3-(4-methoxyphenyl)propoxy, 2-(4-ethoxyphenyl)ethoxy, 3-(2-methoxyphenyl)propoxy, 2-(4-tert-butoxyphenyl)hexyloxy, 6-(4-tert-butoxyphenyl)hexyloxy, 6-(4-hexyloxyphenyl)hexyloxy, and the like.

The halogen-substituted lower alkyl group includes lower alkyl groups having one to three halogen atoms as a substituent.

The $C_3$–$C_8$ cycloalkyloxy which may optionally be substituted by a hydroxy group includes cycloalkyloxy groups having 3 to 8 carbon atoms which have one to three substituents of a hydroxy group, such as 1-hydroxycyclopropyloxy, 1-hydroxycyclobutyloxy, 1-hydroxycyclopentyloxy, 1-hydroxycyclohexyloxy, 1,2-dihydroxycyclohexyloxy, 1,2,3-trihydroxycyclohexyloxy, 1-hydroxycycloheptyloxy, 1-hydroxycyclooctyloxy, and the like.

The lower alkoxy group substituted by a $C_3$–$C_8$ cycloalkyl group having optionally a hydroxy substituent includes lower alkoxy groups which are substituted by the above mentioned $C_3$–$C_8$ cycloalkyl groups having optionally one to three hydroxy substituents.

The imidazolyl(lower)alkyl group includes straight chain or branched chain alkyl groups having 1 to 6 carbon atoms which are substituted by an imidazolyl group, such as 1-imidazolylmethyl, 1-(1-imidazolyl)ethyl, 2-(1-imidazolyl)propyl, 2-(2-imidazolyl)isopropyl, 3-(1-imidazolyl)butyl, 3-(2-imidazolyl)isobutyl, 2-(1-imidazolyl)-tert-butyl, 5-(1-imidazolyl)pentyl, 6-(1-imidazolyl)hexyl, and the like.

The imidazolyl(lower)alkoxy group includes straight chain or branched chain alkoxy groups having 1 to 6 carbon atoms which are substituted by an imidazolyl group, such as 1-imidazolylmethoxy, 1-(1-imidazolyl)ethoxy, 2-(1-imidazolyl)propoxy, 2-(2-imidazolyl)isopropoxy, 3-(1-imidazolyl)butoxy, 3-(2-imidazolyl)isobutyloxy, 2-(1-imidazolyl)-tert-butyloxy, 5-(1-imidazolyl)pentyloxy, 6-(1-imidazolyl)hexyloxy, and the like.

The lower alkylenedioxy group includes alkylenedioxy groups having 1 to 4 carbon atoms, such as methylenedioxy, ethylenedioxy, trimethylenedioxy, tetramethylenedioxy, and the like.

The lower alkylene group includes straight chain or branched chain alkylene groups having 1 to 6 carbon atoms includes methylene, ethylene, trimethylene, tetramethylene, pentamethylene, hexamethylene, 2,2-dimethyltrimethylene, 2-methyltrimethylene, methylmethylene, and the like.

The lower alkyleneoxy group includes straight chain or branched chain alkyleneoxy groups having 1 to 6 carbon atoms, such as methyleneoxy, ethyleneoxy, trimethyleneoxy, tetramethyleneoxy, pentamethyleneoxy, hexamethyleneoxy, 2,2-dimethyltrimethyleneoxy, 2-methyltrimethyleneoxy, methylmethyleneoxy, and the like.

The lower alkenylene group includes straight chain or branched chain alkenylene groups having 2 to 6 carbon atoms, such as vinylene, propenylene, 1-methylvinylene, 2-butenylene, 3-pentenylene, 2-hexenylene, and the like.

The phenylcarboxylic acid derivative having a hetero ring of the formula (1) of this invention can be prepared by various processes using various starting compounds. The examples of the processes are illustrated below with reference to reaction schemes.

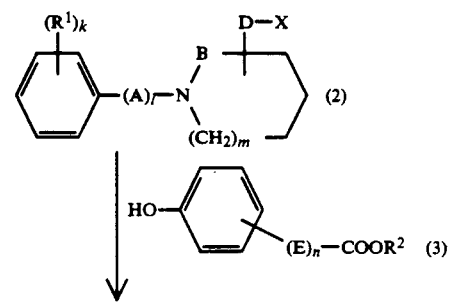

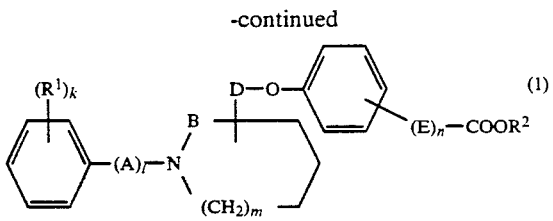

(1)

wherein A, B, D, E, $R^1$, $R^2$, K, l, m and n are as defined above, and X is a halogen atom, a lower alkanesulfonyloxy group having optionally a substituent, or an arylsulfonyloxy group having optionally a substituent.

According to the above Reaction Scheme-1, the compound of the formula (2) and the compound of the formula (3) are reacted in an appropriate inert solvent in the presence of a basic compound to give the desired compound of the formula (1) of this invention.

In the compound of the above formula (2), the halogen atom shown as X includes the same as defined above, the lower alkanesulfonyloxy group having optionally a substituent includes alkanesulfonyloxy groups having 1 to 6 carbon atoms and being optionally substituted by a halogen atom, such as methanesulfonyloxy, ethanesulfonyloxy, propanesulfonyloxy, trifluoromethanesulfonyloxy, etc., and the arylsulfonyloxy group having optionally a substituent includes arylsulfonyloxy groups being optionally substituted by an alkyl group having 1 to 6 carbon atoms, a halogen atom or a nitro group, such as benzenesulfonyloxy, toluenesulfonyloxy, p-chlorobenzenesulfonyloxy, p-nitrobenzenesulfonyloxy, etc.

In the process of the above Reaction Scheme-1, the inert solvent includes various solvents which do not give any bad effect on the reaction, for example, ethers such as diethyl ether, tetrahydrofuran (THF), dioxane, etc.; halogenated hydrocarbons such as dichloromethane, dichloroethane, chloroform, carbon tetrachloride, etc.; aromatic hydrocarbons such as benzene, toluene, xylene, etc.; amines such as pyridine, piperidine, triethylamine, etc.; aliphatic hydrocarbons such as hexane, heptane, etc.; alcohols such as methanol, ethanol, propanol, etc.; aprotic polar solvents such as dimethylformamide (DMF), dimethylacetamide (DMA), dimethylsulfoxide (DMSO), hexamethylphosphoric triamide (HMPA), etc.; carbon disulfide; and the like. The basic compound includes, for example, organic basic compounds such as tertiary amines (e.g. triethylamine, pyridine, etc.) and inorganic basic compounds such as alkali metal carbonates (e.g. sodium carbonate, potassium carbonate, etc.), alkali metal hydrogen carbonates (e.g. sodium hydrogen carbonate, potassium hydrogen carbonate, etc.), alkali metal hydroxides (e.g. sodium hydroxide, potassium hydroxide, etc.), alkali metals (e.g. sodium, potassium, etc.), alkali metal hydrides (e.g. sodium hydride, etc.).

The compound of the formula (3) is usually used in an amount of about 1 to 5 moles, preferably about 1 to 2 moles, to 1 mole of the compound of the formula (2), and the basic compound is usually used in an amount of about 1 to 100 moles, preferably about 1 to 3 moles, to 1 mole of the compound of the formula (2).

The above reaction is usually carried out at about 0° to 200° C., preferably at room temperature—about 120° C., for about 20 minutes to about 72 hours, preferably about 30 minutes to about 48 hours.

In the above Reaction Scheme-1, the compounds of the formula (1) wherein $R^1$ is a lower alkoxy group or a phenyl(lower)alkoxy group which may optionally be substituted by a halogen atom or a lower alkyl group on the phenyl ring can also be prepared by subjecting the compound of the formula (1) wherein $R^1$ is a hydroxy group to the ether bond-forming reaction under the same conditions as in the Reaction Scheme-1.

On the other hand, the compounds of the formula (1) wherein $R^1$ is a hydroxy group can also be prepared by subjecting the compound of the formula (1) wherein $R^1$ is a benzyloxy group which may optionally be substituted by a halogen atom or a lower alkyl group on the phenyl ring (excepting that E is not a lower alkenylene) to a catalytic reduction.

The catalytic reduction can be carried out in an inert solvent with an appropriate catalyst. The catalyst used for the catalytic reduction includes, for example, platinum catalysts such as platinum oxide, platinum black, platinum wire, platinum plate, sponge platinum, colloidal platinum, etc.; palladium catalysts such as palladium black, palladium chloride, palladium oxide, palladium-carbon, palladium-barium sulfate, palladium-barium carbonate, sponge palladium, etc.; nickel catalysts such as reduced nickel, nickel oxide, Raney nickel, etc.; cobalt catalysts such as reduced cobalt, Raney cobalt, etc.; iron catalysts such as reduced iron, Raney iron, etc.; copper catalysts such as reduced copper, Raney copper, etc.; and the like. The inert solvent includes various solvents which do not give any bad effect on the reaction, for example, ethers such as dimethyl ether, diethyl ether, THF, dioxane, anisole, etc.; halogenated hydrocarbons such as dichloromethane, dichloroethane, chloroform, carbon tetrachloride, etc.; aromatic hydrocarbons such as benzene, toluene, xylene, etc.; amines such as pyridine, piperidine, triethylamine, etc.; aliphatic hydrocarbons such as hexane, heptane, octane, etc.; alcohols such as methanol, ethanol, propanol, etc.; acetic acid esters such as ethyl acetate, methyl acetate, etc.; aprotic polar solvents such as DMF, DMSO, HMPA, etc.; water; and the like, or a mixture of water with the above organic solvents. The catalyst for the catalytic reduction is usually used in a catalystic to greatly excess amount. The reaction temperature is usually in the range of about 0° to 200° C., preferably about 0° to 100° C., and the reaction is usually completed in about 30 minutes to about 48 hours, preferably about 30 minutes to about 24 hours.

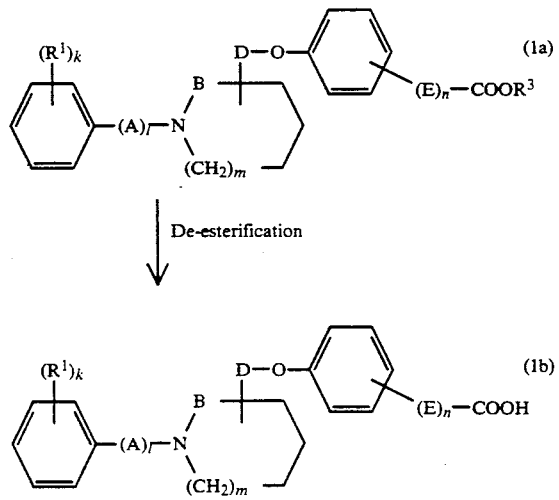

wherein A, B, D, E, $R^1$, k, l, m and n are as defined above, and $R^3$ is a lower alkyl group.

According to the above Reaction Scheme-2, the compound of the formula (1a) of this invention is subjected to de-esterification to give the desired compound of the formula (1b) of this invention.

The de-esterification reaction is carried out by reacting the compound of the formula (1a) with an acidic compound or a basic compound in an appropriate inert solvent.

In the process of the above Reaction Scheme-2, the inert solvent includes various solvents which do not give any bad effect on the reaction, for example, ethers such as dimethyl ether, diethyl ether, THF, dioxane, anisole, etc.; halogenated hydrocarbons such as dichloromethane, dichloroethane, chloroform, carbon tetrachloride, etc.; aromatic hydrocarbons such as benzene, toluene, xylene, etc.; amines such as pyridine, piperidine, triethylamine, etc.; aliphatic hydrocarbons such as hexane, heptane, octane, etc.; alcohols such as methanol, ethanol, propanol, etc.; acetic acid esters such as ethyl acetate, methyl acetate, etc.; aprotic polar solvents such as DMF, DMSO, HMPA, etc.; carbon disulfide; water; and the like, or a mixture of water with the above organic solvents. The acidic compound includes, for example, Lewis acids such as anhydrous aluminum chloride, stannic chloride, titanium tetrachloride, boron trichloride, boron trifluoride-ethyl ether complex, zinc chloride, etc.; inorganic acids such as hyrochloric acid, nitric acid, sulfuric acid, etc.; organic acids such as trichloroacetic acid, trifluoroacetic acid, methanesulfonic acid, acetic acid, etc.; acid type ion exchange resins; and the like. The basic compound includes, for example, organic bases such as trialkylamines (e.g. triethylamine, tributylamine, etc.), pyridine, picoline, 1,5-diazabicyclo[4.3.0]nonene-5 (DBN), 1,8-diazabicyclo[5.4.0]undecene-7 (DBU), 1,4-diazabicyclo[2.2.2]octane (DABCO), etc.; and inorganic bases such as alkali metal hydroxides (e.g. sodium hydroxide, potassium hydroxide, etc.), alkali metal carbonates (e.g. sodium carbonate, potassium carbonate, etc.); and alkali metal hydrogen carbonates (e.g. sodium hydrogen carbonate, potassium hydrogen carbonate, etc.).

The above acidic compound and basic compound are usually used in an amount of about 1 to 100 moles, preferably about 1 to 20 moles, to 1 mole of the compound of the formula (1a). The above reaction is usually carried out at about $-20°$ to 150° C., preferably about $-10°$ to 120° C., for about 30 minutes to about 48 hours, preferably about 1 to 24 hours.

The desired compounds of this invention can be prepared by the processes shown in the above reaction schemes.

The starting compounds of the formula (2) in the above Reaction Scheme-1 include novel compounds and can be prepared by the processes as shown in the following Reaction Scheme-3.

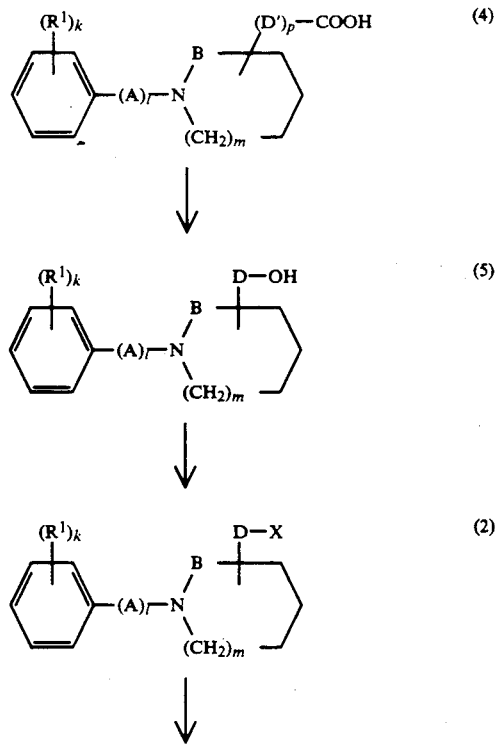

[Reaction Scheme-3]

wherein A, B, D, $R^1$, k, l, m and X are as defined above, and D' is a lower alkylene having one less carbon atom than that of D in the main chain, and p is 0 or 1.

According to the above Reaction Scheme-3, the compound of the formula (5) can be prepared by reducing the compound of the formula (4).

The reducing reaction can be carried out by a conventional method, which conditions may vary depending on the kinds of the substituents of $R^1$ and the group B of the compound (4).

That is, in case of converting the starting compound (4) wherein the group B is a carbonyl group into the corresponding compound (5) wherein said group B is maintained as it stands, the reducing reaction is preferably carried out by previously esterifying the compound (4) or previously converting the compound (4) into an acid halide, followed by the reducing reaction.

The esterification is carried out by reacting the compound (4) with an alcohol in an appropriate inert solvent in the presence of an acidic catalyst. The inert solvent used therein includes various solvents which do not give any bad effect on the reaction, for example, ethers such as diethyl ether, THF, dioxane, etc.; halogenated hydrocarbons such as dichloromethane, dichloroethane, chloroform, etc.; aromatic hydrocarbons such as benzene, toluene, xylene, etc.; aliphatic hydrocarbons such as hexane, heptane, etc.; alcohols such as methanol, ethanol, propanol, etc.; or a mixture of these solvents. The acidic catalyst includes, for example, Lewis acids such as aluminum chloride, stannic chloride, titanium tetrachloride, boron trichloride, boron trifluoride-ethyl ether complex, zinc chloride, etc.; inorganic acids such as hydrochloric acid, nitric acid, sulfuric acid, etc.; organic acids such as trichloroacetic acid, trifluoroacetic acid, methanesulfonic acid, acetic acid, etc.; acid type ion exchange resins; and the like.

The alcohol to be reacted with the compound (4) includes methanol, ethanol, propanol, etc, which can also act as a solvent. The alcohol is usually used at least in an equimolar amount, preferably in an amount of about 1 to 30 moles to 1 mole of the compound of the formula (4), and the reaction is usually carried out at room temperature to a reflux temperature of the solvent, for about 1 to 72 hours, preferably about 3 to 24 hours.

The subsequent reducing reaction is carried out by a conventional method, for instance, by using an appropriate reducing agent in an appropriate solvent. The solvent includes the conventional inert solvents, for example, ethers such as diethyl ether, THF, dioxane, etc.; aromatic hydrocarbons such as benzene, toluene, xylene, etc.; aliphatic hydrocarbons such as hexane, heptane, etc.; alcohols such as methanol, ethanol, propanol, etc.; and the like, or a mixture of these solvents. The reducing agent includes, for example, metal hydrides such as sodium cyanoboron hydride, sodium boron hydride, lithium aluminum hydride, etc.; borane, and the like, preferably sodium boron hydride which is used while adding thereto methanol dropwise. These reducing agents are usually used in an amount of about 0.1 to 5 moles, preferably about 0.5 to 2 moles, to 1 mole of the starting ester, and the reducing reaction is usually carried out at about $-50°$ C. to a reflux temperature of the solvent for about 10 minutes to about 24 hours, preferably about 1 to 5 hours. When the reducing reaction is carried out while adding dropwise methanol, the methanol is usually used in an amount of about 1 to 50 moles, preferably about 4 to 20 moles, to 1 mole of the reducing agent.

In the process of previously converting the compound of the formula (4) into an acid halide, followed by subjecting to the reducing reaction, the converting reaction into an acid halide is carried out by a conventional method. In more detail, the reaction is carried out by using a halogenating agent such as a halogen molecule (e.g. chlorine, bromine, iodine, etc.), a thionyl halide (e.g. thionyl chloride, thionyl bromide, etc.), and the like, in an appropriate solvent such as halogenated hydrocarbons (e.g. methylene chloride, 1,2-dichloroethane, chloroform, etc.), aromatic hydrocarbons (e.g. benzene, xylene, toluene, etc.), ethers (e.g. THF, dioxane, etc.), and the like. The above halogenating agent is used at least in an equimolar amount, preferably in an amount of 1 to 2 moles, to 1 mole of the starting compound. The reaction is usually carried out at about $-10°$ to $150°$ C., preferably at about $0°$ C. to about $100°$ C., for about 1 to 20 hours, preferably about 1 to 10 hours.

The reducing reaction of the acid halide thus prepared is carried out by a conventional method, for example, with a conventional reducing agent in an appropriate solvent. The solvent includes various conventional solvents, for example, ethers such as diethyl ether, THF, dioxane, etc.; halogenated hydrocarbons such as dichloromethane, dichloroethane, chloroform, carbon tetrachloride, etc.; aromatic hydrocarbons such as benzene, toluene, xylene, etc.; aliphatic hydrocarbons such as hexane, heptane, etc.; aprotic polar solvents such as DMF, DMSO, HMPA, etc.; and the like, or a mixture of these solvents. The reducing agent includes, for example, metal hydrides such as sodium cyanoboron hydride, sodium boron hydride, lithium aluminum hydride, and the like, preferably sodium boron hydride. These reducing agents are usually used in an amount of about 0.1 to 5 moles, preferably about 0.5 to 3 moles, to 1 mole of the starting acid halide, and the reaction is usually carried out at about $-50°$ C. to a room temperature, preferably about $-10°$ C. to about $10°$ C., for about 10 minutes to about 8 hours, preferably about 30 minutes to about 2 hours.

In the Reaction Scheme-3, the starting compound of the formula (4) wherein the group B is a carbonyl group may be converted into the compound of the formula (5) by simultaneously reducing the group B into a methylene group together with reduction of the carboxyl group. The reducing reaction can be carried out, for example, in above-mentioned various inert solvents with a reducing agent, for example, metal hydrides such as sodium cyanoboron hydride, sodium boron hydride, lithium aluminum hydride, etc.; borane, and the like, preferably lithium aluminm hydride. These reducing agents are usually used in an amount of about 0.1 to 100 moles, preferably about 1 to 10 moles, to 1 mole of the starting compound, and the reaction is usually carried out at about $-20°$ to $180°$ C., preferably about $0°$ to $100°$ C., for about 10 minutes to about 24 hours, preferably about 3 to 20 hours.

In the Reaction Scheme-3, the reducing of a carboxyl group of the compound of the formula (4) wherein the group B is a methylene group is carried out in the same manner as in case of converting the starting compound (4) wherein the group B is a carbonyl group into the corresponding compound (5) wherein said group B is maintained as it stands, by previously esterifying the compound (4) or previously converting the compound (4) into an acid halide, followed by the reducing reaction as mentioned hereinabove.

In the Reaction Scheme-3, when a compound of the formula (4) wherein $R^1$ is a hydroxy group is used in the reaction of esterifying the compound (4) and then reducing to give the compound (5), the esterified compound may be etherified to convert it into the corresponding compound wherein $R^1$ is a lower alkoxy group or a phenyl(lower)alkoxy group having optionally a substituent of a halogen atom or a lower alkyl group on the phenyl ring and thereafter subjecting to the reducing reaction. The above reaction of converting the $R^1$ group (i.e. etherifying reaction) can be carried out under the same conditions as in the ether-bond forming reaction in the above Reaction Scheme-1.

The desired compound of the formula (5) can be obtained as above.

According to the Reaction Scheme-3, the hydroxy group of the compound of the formula (5) thus obtained is converted into the X group to give the desired compound of the formula (2).

The converting reaction of the compound (5) having a hydroxy group into the compound (2) having the X group is usually carried out by reacting the compound (5) with a sulfonic acid compound or a reactive derivative at the sulfo group thereof or with a halogenating agent in a solvent.

The reaction of the compound (5) with a sulfonic acid compound or a reactive derivative at the sulfo group thereof is carried out by reacting the compound (5) with a sulfonic acid compound corresponding to the sulfonyloxy group (as the X group) or a reactive derivative at the sulfo group thereof (e.g. halides such as chloride, bromide, etc., or acid anhydrides) in a solvent. The solvent used therein includes aromatic hydrocarbons such as benzene, toluene, xylene, etc.; ethers such as diethyl ether, THF, etc.; halogenated hydrocarbons such as methylene chloride, chloroform, dichloroethane, etc.; aprotic polar solvents such as DMF, DMSO, HMPA, etc.; acetonitrile; and the like.

The above sulfonic acid compound or a reactive derivative at the sulfo group thereof is usually used at least in an equimolar amount, preferably in an amount of about 1 to 1.5 mole, to 1 mole of the compound (5). The reaction is preferably carried out in the presence of a basic compound. The basic compound includes alkali metal hydroxides (e.g. sodium hydroxide, potassium hydroxide, etc.), alkali metal carbonates or hydrogen carbonates (e.g. sodium carbonate, potassium carbonate, sodium hydrogen carbonate, etc.), and organic basic compounds (e.g. triethylamine, pyridine, N,N-dimethylaniline, DBN, DABCO, DBU, etc.). The reaction is usually carried out at about −10° C. to about 100° C., preferably about 0° C. to room temperature, for about 1 to 20 hours, preferably about 1 to 10 hours.

The compound of the formula (2) wherein X is a halogen atom can be prepared by reacting the compound (5) with a halogenating agent. The halogenating agent used in this reaction includes, for example, halogen molecules (e.g. chlorine, bromine, iodine, etc.), thionyl halides (e.g. thionyl chloride, thionyl bromide, etc.) and the like. The reaction is usually carried out in a solvent. The solvent includes halogenated hydrocarbons (e.g. methylene chloride, 1,2-dichloroethane, chloroform, etc.), ethers (e.g. tetrahydrofuran, dioxane, etc.), and the like. The halogenating agent is usually used at least in an equimolar amount, preferably in an amount of 1 to 2 moles to 1 mole of the compound (5). The reaction is usually carried out at about −10° to 100° C., preferably 0° to 50° C., for about 1 to 20 hours, preferably about 1 to 10 hours.

The starting compound of the formula (4) used in the above Reaction Scheme-3 includes novel compounds, and can be prepared by the processes as shown in the following Reaction Schemes-4 and -5.

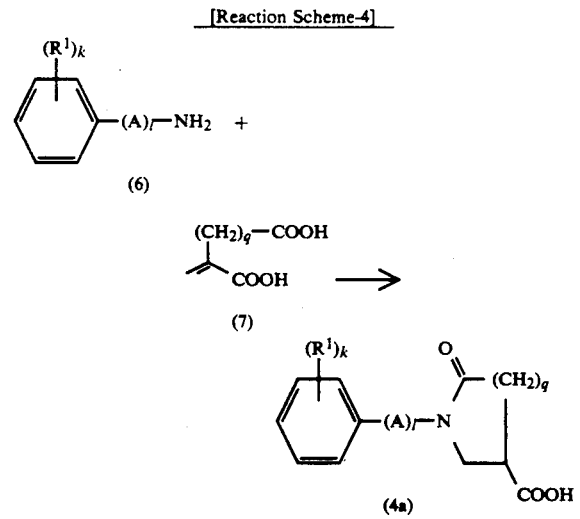

[Reaction Scheme-4]

wherein A, $R^1$, k and l are as defined above, and q is 1 or 2.

According to the above Reaction Scheme-4, the compound of the formula (6) and the compound of the formula (7) are reacted to give the desired compound of the formula (4a).

The reaction is carried out in an inert solvent or without using a solvent (under the condition of melting of the starting compounds), preferably without using a solvent. The inert solvent used therein includes, for example, ethers such as dimethyl ether, diethyl ether, THF, dioxane, anisole, etc.; aromatic hydrocarbons such as benzene, toluene, xylene, etc.; alcohols such as methanol, ethanol, propanol, etc.; aprotic polar solvents such as DMF, DMSO, HMPA, etc.; water; and the like, or a mixture of these solvents. The compound (7) is usually used in an amount of about 1 to 1.5 mole, preferably about 1 mole, to 1 mole of the compound (6). The reaction is usually carried out at about 100° to 200° C., preferably about 120° to 150° C., for about 1 to 24 hours, preferably about 2 to 5 hours (provided that when the reaction is carried out at a temperature higher than the boiling point of the solvent, it is carried out under a pressure).

The compounds of the formula (6) wherein $R^1$ is a lower alkoxy group or a phenyl(lower)alkoxy group which may optionally have a substituent selected from a halogen atom and a lower alkyl group on the phenyl ring (excepting benzyloxy group) may be prepared, for example, by subjecting the corresponding nitro compound wherein $R^1$ is a hydroxy group to the same reaction as shown in Reaction Scheme-1 in order to convert the hydroxy group into a specific $R^1$ group and then reducing the nitro group thereof to an amino group by subjecting it to a catalytic reduction as shown in Reaction Scheme-1.

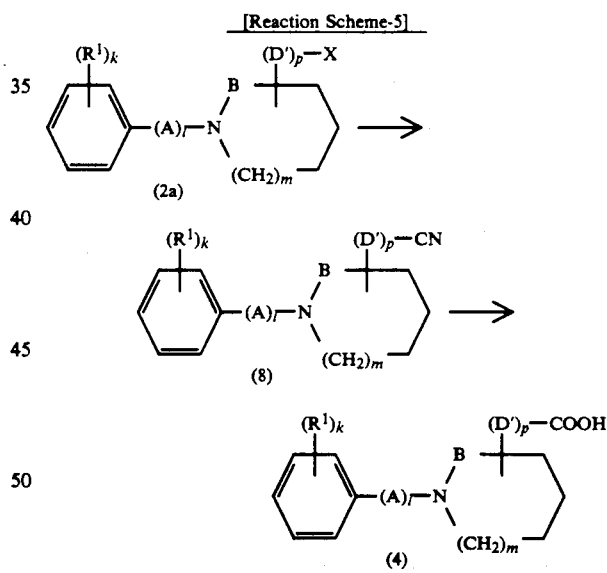

[Reaction Scheme-5]

wherein A, B, D', $R^1$, k, l m, p and X are as defined above.

According to the above Reaction Scheme-5, the compound of the formula (2a) is reacted with a cyanide compound to give the compound of the formula (8), and then the compound (8) is hydrolized to give the desired compound of the formula (4).

The reaction of preparing the compound (8) from the compound (2a) is usually carried out in an appropriate inert solvent by using a cyanide compound. The inert solvent used therein includes, for example, ethers such as dimethyl ether, diethyl ether, THF, dioxane, anisole, etc.; aromatic hydrocarbons such as benzene, toluene, xylene, etc.; alcohols such as methanol, ethanol, propanol, etc.; aprotic polar solvents such as DMF, DMSO, HMPA, etc.; and the like. The cyanide compound used therein includes, for example sodium cyanide, potassium cyanide, calcium cyanide, copper cyanide, silver cyanide, potassium silver cyanide, mercury cyanide, and the like. The cyanide compound is usually used in an amount of about 1 to 5 moles, preferably about 1 to 2 moles, to 1 mole of the compound of the formula (2a). The above reaction is usually carried out at about 0° to 200° C., preferably at room temperature to about 120° C., for about 1 to 72 hours, preferably about 3 to 24 hours.

The subsequent hydrolysis can be carried out under the same conditions as in the de-esterification as shown in the above Reaction Scheme-2.

The compound of the formula (5) in the above Reaction Scheme-3 may also be prepared by other processes as follows.

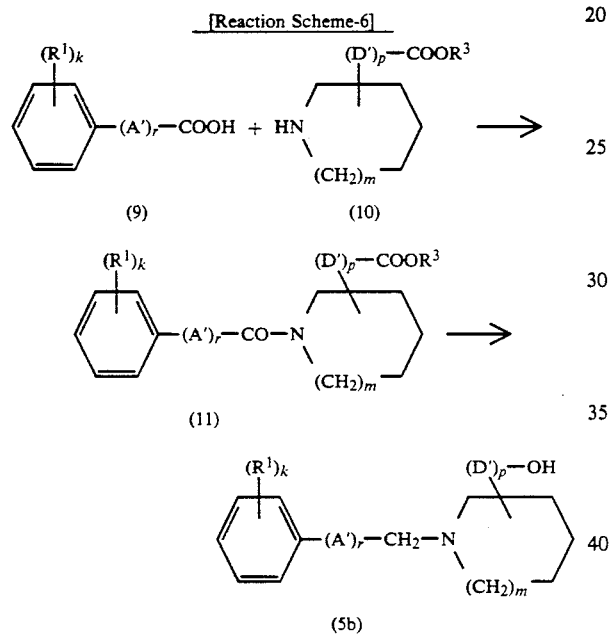

wherein D', $R^1$, k, m and p are as defined above, A' is a lower alkylene group having one less carbon atom in the main chain than that of the group A or a lower alkyleneoxy group having one less carbon atoms in the main chain than that of the group A, r is 0 or 1, and $R^3$ is a lower alkyl group.

According to the above Reaction Scheme-6, the carboxylic acid compound of the formula (9) and the compound of the formula (10) are reacted by a conventional amido bond producing reaction to give the compound of the formula (11) and then the compound of the formula (11) is subjected to a reducing reaction to give the desired compound of the formula (5b).

The amido bond producing reaction can easily be carried out by the various conventional processes, for example, a mixed acid anhydride process, an activated ester process, a process using a condensation agent, a carboxylic acid anydride process, a process of carrying at a high temperature under high pressure, an acid halide process, and the like.

The acid halide process is explained in detail below. This process can be carried out by converting the compound of the formula (9) into an acid halide compound, and reacting the acid halide with the compound of the formula (10) in an appropriate solvent in the presence of a dehydrohalogenation agent. The dehydrohalogenation agent includes conventional agents, for example, sodium hydrogen carbonate, sodium carbonate, potassium carbonate, pyridine, triethylamine, and the like. The solvent includes also conventional ones, for example, benzene, chloroform, methylene chloride, dioxane, THF, and the like. The acid halide used in the above reaction is usually used at least in about equimolar amount, preferably in an amount of about 1 to 3 moles, to 1 mole of the compound (10). The reaction temperature is usually in the range of −30° to 100° C., preferably room temperature to about 80° C., and the reaction is usually completed in about 20 minutes to about 20 hours.

The reaction for preparing the compound of the formula (5b) from the compound (11) thus obtained is carried out under the same reducing reaction conditions as in the reducing reaction of the compound of the formula (4) wherein the group B is a carbonyl group to prepare the compound of the formula (5) wherein B is a methylene group as shown in the above Reaction Scheme-3.

The compounds of the formula (3) in the above Reaction Scheme-1 also include novel compounds, which can be prepared by a process as shown in the following Reaction Scheme-7.

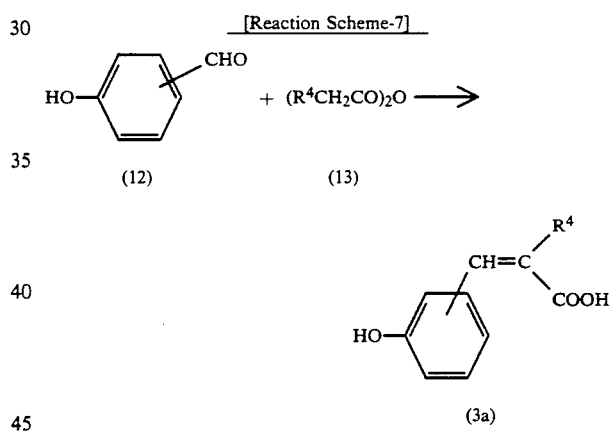

wherein $R^4$ is hydrogen atom or a lower alkyl group.

According to the above Reaction Scheme-7, the compound of the formula (12) is reacted with an aliphatic carboxylic acid anhydride of the formula (13) or an alkali metal salt (e.g. sodium or potassium salt) thereof with heating (Perkin reaction) to give the compound of the formula (3a).

In this reaction, the compound (13) or a salt thereof is usually used in an amount of about 1 to 100 moles, preferably about 1 to 20 moles, to 1 mole of the compound of the formula (12). This reaction is usually carried out at about 0° to 200° C., preferably at room temperature to about 150° C., for about 30 minutes to about 96 hours, preferably about 1 to 48 hours.

The compounds of the formula (1) can be converted into various compounds wherein $R^1$ and E have various groups as mentioned hereinabove.

Among the compounds of the formula (1) and the intermediate compounds for preparing the same as shown in the above reaction schemes, the compounds having the following $R^1$ groups can be converted into the corresponding desired compounds or intermediates having the desired $R_1$ groups by the following various reactions.

That is, the compounds wherein $R^1$ is a hydroxy group can be converted into the compounds wherein $R^1$ is a lower alkylsulfonyloxy group by subjecting it to the reaction as shown in the above Reaction Scheme-3.

The compounds wherein $R^1$ is a lower alkanoylamino group can be converted into the compounds having the corresponding amino group by a conventional amide hydrolysis reaction.

The hydrolysis can be carried out, for example, by using an acid catalyst as used in the de-esterification reaction as shown in the above Reaction Scheme-2 in an appropriate inert solvent. The inert solvent used therein includes various solvents which do not give any bad effect on the reaction, for example, ethers such as dimethyl ether, diethyl ether, THF, dioxane, anisole, etc.; halogenated hydrocarbons such as dichloromethane, dichloroethane, chloroform, carbon tetrachloride, etc.; aromatic hydrocarbons such as benzene, toluene, xylene, etc.; aliphatic hydrocarbons such as hexane, heptane, octane, etc.; alcohols such as methanol, ethanol, propanol, etc.; aprotic polar solvents such as DMF, DMSO, HMPA, etc.; water; and the like, or a mixture of water with the above organic solvents, among which preferred are alcohols which have the same alkyl group as the group $R^2$ in the starting compounds. The reaction temperature and reaction time are the same as those in the above-mentioned de-esterification reaction. By such a hydrolysis, the desired compounds wherein $R^1$ is an amino group can be obtained.

In the above hydrolysis reaction, when the solvent used therein is a solvent other than the alcohols which have the same alkyl group as the group $R^2$ in the starting compounds, de-esterification of $R^2$ group occurs simultaneously with the deacylation of the $R^1$ group to give the corresponding compounds wherein $R^1$ is an amino group and $R^2$ is a carboxyl group. This reaction can also be used for the preparation of the desired compounds of the present invention and the intermediates.

The compounds wherein $R^1$ is a phenyl(lower)alkoxy(lower)alkoxy group can be converted into the corresponding compounds wherein $R^1$ is a hydroxy(lower)alkoxy group by subjecting to the same catalytic reduction as used in the reaction shown in Reaction Scheme-1.

The compounds wherein $R^1$ is a hydroxy group can be converted into the corresponding compounds wherein $R^1$ is the desired groups by reacting the compounds with a compound of the formula: R-X (wherein R is the same groups as $R^1$ other than hydroxy group and X is a halogen atom) under the same conditions as in the ether bond-forming reaction as shown in the above Reaction Scheme-1. In this reaction, the compound of the formula: R-X is usually used in an amount of about 1 to 30 moles, preferably about 1 to 10 moles, to 1 mole of the starting compound.

Moreover, the compounds wherein $R^1$ is a hydroxy group can also be converted into the desired compounds wherein $R^1$ is a hydroxy-substituted lower alkoxy group by reacting them with an appropriate epoxy compound (i.e. an alkene oxide). The reaction is carried out, for example, in an appropriate inert solvent in the presence of a basic compound. The inert solvent used therein includes various solvents which do not give any bad effect on the raction, for example, ethers such as diethyl ether, THF, dioxane, etc.; halogenated hydrocarbons such as dichloromethane, dichloroethane, chloroform, carbon tetrachloride, etc.; aromatic hydrocarbons such as benzene, toluene, etc.; amines such as pyridine, piperidine, triethylamine, etc.; aliphatic hydrocarbons such as hexane, heptane, etc.; alcohols such as methanol, ethanol, propanol, etc.; aprotic polar solvents such as DMF, DMA, DMSO, HMPA, etc.; carbon disulfide; and the like. The basic compound includes, for example, organic basic compounds such as tertiary amines (e.g. triethylamine, pyridine, etc.), inorganic basic compounds such as alkali metal carbonates (e.g. sodium carbonate, potassium carbonate, etc.), alkali metal hydrogen carbonates (e.g. sodium hydrogen carbonate, potassium hydrogen carbonate, etc.), alkali metal hydroxides (e.g. sodium hydroxide, potassium hydroxide, etc.), alkali metal alkoxides (e.g. sodium methoxide, sodium ethoxide, potassium methoxide, potassium ethoxide, potassium tert-butoxide, etc.), alkali metals (e.g. metal sodium, metal potassium etc.), and alkali metal hydrides (e.g. sodium hydride, etc.), and the like. The epoxy compound is usually used in an amount of about 1 to 100 moles, preferably about 1 to 30 moles, to 1 mole of the starting compound wherein $R^1$ is a hydroxy group, and the basic compound is usually used in an amount of about 0.01 to 10 moles, preferably about 0.1 to 3 moles, to 1 mole of the above starting compound. This reaction is usually carried out at about 0° to 200° C., preferably at room temperature to about 120° C., for about 5 hours to about 10 days, preferably about 1 to 7 days.

The compounds wherein $R^1$ is a hydroxy-substituted lower alkoxy group can be converted into the corresponding compounds wherein $R^1$ is a lower alkylsulfonyloxy(lower)alkoxy group by subjecting them to the same reaction as shown in Reaction Scheme-3.

The compounds wherein $R^1$ is a lower alkylsulfonyloxy(lower)alkoxy group or a halogen-substituted lower alkyl group can be converted into the corredsponding compounds wherein $R^1$ is an imidazolyl(lower)alkyl group or an imidazolyl(lower)alkoxy group respectively by reacting them with imidazole. This reaction can be carried out in a similar manner as in the ether bond-forming reaction as shown in Reaction Scheme-1. The compounds wherein $R^1$ is a halogen-substituted lower alkyl group used in the above reaction can easily be prepared by halogenating the corresponding compounds wherein $R^1$ is a lower alkyl group by a conventional halogenating process.

The compounds wherein $R^1$ is a hydroxy group can be converted into the corresponding compounds wherein $R^1$ is a tert-butoxy group by reacting them with O-tert-butyl-N,N'-dicyclohexylisourea under the following conditions. The alkylation reaction can be carried out in an appropriate solvent, for example, ethers such as diethyl ether, THF, dioxane, etc.; halogenated hydrocarbons such as dichloromethane, dichloroethane, chloroform, carbon tetrachloride, etc.; aromatic hydrocarbons such as benzene, toluene, xylene, etc.; aliphatic hydrocarbons such as hexane, heptane, etc.; aprotic polar solvents such as DMF, DMA, DMSO, HMPA, etc.; and the like. The O-tert-butyl-N,N'-dicyclohexylisourea is usually used in an amount of about 1 to 30 moles, preferably about 1 to 5 moles, to 1 mole of the compound wherein $R^1$ is a hydroxy group. The reaction is usually carried out at about 0° to 150° C., preferably at room temperature to about 80° C.

Among the phenylcarboxylic acid derivatives having a hetero ring of the formula (1) of this invention, the compounds having a basic group can easily be converted into acid addition salts thereof by treating with a pharmaceutically acceptable acid. The acid includes, for example, inorganic acids such as hydrochloric acid, sulfuric acid, phosphoric acid, hydrobromic acid, etc., and organic acids such as oxalic acid, maleic acid, fumaric acid, malic acid, tartaric acid, citric acid, benzoic acid, acetic acid, p-toluenesulfonic acid, ethanesulfonic acid, etc.

Among the phenylcarboxylic acid derivatives having a hetero ring of the formula (1) of this invention, the compounds having an acidic group can easily be converted into salts by treating with a pharmaceutically acceptable basic compound. The basic compound includes, for example, metal hydroxides such as sodium hydroxide, potassium hydroxide, calcium hydroxide, etc., alkali metal carbonates or hydrogen carbonates such as sodium carbonate, potassium hydrogen carbonate, sodium hydrogen carbonate, etc.

The compounds of this invention thus obtained can easily be isolated and purified by conventional isolation methods. The isolation methods are, for example, extraction with a solvent, dilution method, recrystallization method, column chromatography, preparative thin layer chromatography, and the like.

The compounds of the formula (1) of this invention may be present in the form of optical isomers, and hence, this invention includes also these isomers. These isomers can easily be resolved by conventional resolution methods, for example, by using an optical resoluting agent.

The derivatives and their salts of this invention are used in the form of a conventional pharmaceutical preparation. The preparation is prepared by using conventional dilutents or carriers such as fillers, thickening agents, binders, wetting agents, disintegrators, surfactants, lubricants, and the like. The pharmaceutical preparations may be selected from various forms in accordance with the desired utilities, and the representative forms are tablets, pills, powders, solutions, suspensions, emulsions, granules, capsules, suppositories, injections (solutions, suspensions, etc.), ointments, and the like. In order to form tablets, there are used carriers such as vehicles (e.g. lactose, white sugar, sodium chloride, glucose, urea, starches, calcium carbonate, kaolin, crystalline cellulose, silicic acid, etc.), binders (e.g. water, ethanol, propanol, simple syrup, glucose solution, starch solution, gelatin solution, carboxymethyl cellulose, shellac, methyl cellulose, potassium phosphate, polyvinylpyrrolidone, etc.), disintegrators (e.g. dry starch, sodium arginate, agar powder, laminaran powder, sodium hydrogen carbonate, calcium carbonate, polyoxyethylene sorbitan fatty acid esters, sodium laurylsulfate, stearic monoglyceride, starches, lactose, etc.), disintegration inhibitors (e.g. white sugar, stearin, cacao butter, hydrogenated oils, etc.), absorption promoters (e.g. quaternary ammonium salts, sodium laurylsulfate, etc.), wetting agents (e.g. glycerin, starches, etc.), adsorbents (e.g. starches, lactose, kaolin, bentonite, colloidal silicates, etc.), lubricants (e.g. purified talc, stearates, boric acid powder, polyethylene glycol, etc.), and the like. Moreover, the tablets may also be in the form of a conventional coated tablet, such as sugar-coated tablets, gelatin-coated tablets, enteric coated tablets, film coating tablets, or double or multiple layer tablets. In the preparation of pills, the carriers include vehicles (e.g. glucose, lactose, starches, cacao butter, hydrogenated vegetable oils, kaolin, talc, etc.), binders (e.g. gum arabic powder, tragacanth powder, gelatin, ethanol, etc.), disintegrators (e.g. laminaran, agar, etc.), and the like. In the preparation of suppositories, the carriers include, for example, polyethylene glycol, cacao butter, higher alcohols, higher alcohol esters, gelatin, semi-synthetic glycerides, and the like. Capsules can be prepared by charging a mixture of the compound of this invention with the above carriers into hard gelatin capsules or soft gelatin capsules in a usual manner. In the preparation of injections, the solutions, emulsions or suspensions are sterilized and are preferably made isotonic with the blood. In the preparation of these forms, there are used diluents such as water, aqueous lactic acid solution, ethyl alcohol, propylene glycol, ethoxylated isostearyl alcohol, polyoxylated isostearyl alcohol, polyoxyethylene sorbitan fatty acid esters, and the like. In this case, the pharmaceutical preparations may also be incorporated with sodium chloride, glucose, or glycerin in an amount sufficient to make them isotonic, and may also be incorporated with solubilizers, buffers, anesthetizing agents. Further, the pharmaceutical preparations may optionally be incorporated with coloring agents, preservatives, perfumes, flavors, sweeting agents, and other medicaments. In the preparations of paste, cream and gel, there may be used diluents such as white vaseline, paraffin, glycerin, cellulose derivatives, polyethylene glycol, silicone, bentonite, and the like.

The amount of the compounds of the formula (1) or their salts of this invention (active ingredient) to be incorporated into the pharmaceutical preparations is not specified but may be selected from a broad range, but is preferably in the range of 1 to 70 % by weight.

The above pharmaceutical preparations may be administered in any method, and suitable method for administration may be determined in accordance with various forms of preparation, ages, sexes and other conditions of the patients, the degree of severity of diseases, and the like. For instance, tablets, pills, solutions, suspensions, emulsions, granules and capsules are administered orally. The injections are intraveneously administered alone or together with a conventional auxiliary liquid (e.g. glucose, amino acid solutions), and further are optionally administered alone in intramuscular, intracutaneous, subcutaneous, or intraperitoneal route. Suppositories are administered in intrarectal route.

The dosage of the above pharmaceutical preparations may be selected in accordance with the usage, ages, sexes and other conditions of the patients, the degree of severity of the diseases, and the like, but is usually in the range of about 0.5 to 100 mg, preferably about 2 to 20 mg, of the active compound of this invention per 1 kg of body weight of the patient per day. The preparation may be administered by dividing into 1 to 4 times per day.

EXAMPLES

This invention is illustrated in detail by the following examples but should not be construed to be limited thereto.

EXAMPLE 1

(1) 1-(4-Tolyl)-5-oxo-3-pyrrolidinecarboxylic acid p-Toluidine (23.05 g) and itaconic acid (28.0 g) are mixed and heated at 130° C. for 1 hour to melt and then allowed to cool. Water (200 ml) is added thereto and the reaction mixture is crushed. The resulting precipitate is collected by filtration, washed with water and recrystallized from a mixed solvent (about 300 ml) of ethyl acetate and hexane [1:3 (v/v)] to give the desired product (45.73 g), m.p. 185°–187° C.

(2) Methyl 1-(4-tolyl)-5-oxo-3-pyrrolidinecarboxylate 1-(4-Tolyl)-5-oxo-3-pyrrolidinecarboxylic acid (45.50 g) is suspended in methylene chloride (460 ml) and thereto are added methanol (50.5 ml) and conc. sulfuric acid (0.77 ml) and the mixture is refluxed for 19 hours. After cooling, the reaction mixture is concentrated under reduced pressure and the resulting residue is neutralized by adding water and aqueous sodium hydrogen carbonate solution thereto. The precipitated crystal is collected by filtration and washed with water to give the desired product (46.07 g), m.p. 71°–74° C.

(3) 1-(4-Tolyl)-4-hydroxymethyl-2-pyrrolidone

Methyl 1-(4-tolyl)-5-oxo-3-pyrrolidinecarboxylate (46.00 g) and sodium boron hydride (5.94 g) are suspended in tetrahydrofuran (460 ml) and to the mixture is added dropwise methanol (46.2 ml) over a period of 1 hour under refluxing. The mixture is further heated for 1 hour. After cooling the reaction mixture, conc. hydrochloric acid (13.7 ml) and water (about 5 ml) are added thereto and then the mixture is concentrated under reduced pressure. Methylene chloride (400 ml) is added to the residue and the insoluble material is removed by filtration. The filtrate is washed with water (about 100 ml). The organic layer is dried over anhydrous magnesium sulfate and concentrated under reduced pressure to give the desired product (39.80 g) as solid.

NMR (CDCl$_3$) δ ppm: 7.44 (d, 2H, J=8.6 Hz), 7.15 (d, 2H, J=8.6 Hz), 4.03–3.53 (m, 4H), 2.78–2.03 (m, 7H).

(4) Methyl 4-[1-(4-tolyl)-2-pyrrolidon-4-yl]methoxybenzoate 1-(4-Tolyl)-4-hydroxymethyl-2-pyrrolidone (39.70 g) is dissolved in methylene chloride (400 ml) and the mixture is cooled with ice. Thereto are added dropwise methanesulfonyl chloride (22.47 ml) and triethylamine (53.59 ml) severally and the mixture is stirred at room temperature for 22 hours. The reaction mixture is concentrated under reduced pressure and thereto is added ethyl acetate (500 ml). The mixture is washed with water three times, dried over anhydrous magnesium sulfate and concentrated under reduced pressure to give an oily mesylate compound (52.75 g).

This mesylate compound is dissolved in dimethylformamide (630 ml) and thereto are added methyl p-hydroxybenzoate (28.33 g) and potassium carbonate (51.45 g). The mixture is heated with stirring at 80° C. for 5 hours. After cooling, the reaction mixture is concentrated under reduced pressure and water (500 ml) is added to the residue. The resulting precipitate is collected by filtration, washed with water and recrystallized from about 20% aqueous methanol (400 ml) to give the desired product (58.74 g), m.p. 110°–112° C.

(5) 4-[1-(4-Tolyl)-2-pyrrolidon-4-yl]methoxybenzoic acid

Methyl 4-[1-(4-tolyl)-2-pyrrolidon-4-yl]methoxybenzoate (58.74 g) and sodium hydroxide (10.40 g) are dissolved in about 20 % aqueous methanol (630 ml) and the mixture is heated with stirring at 60° C. for 14 hours. After cooling, the reaction mixture is concentrated under reduced pressure to about the half volume thereof and thereto are added water (130 ml) and conc. hydrochloric acid (22.6 ml). The precipitated crystal is collected by filtration, washed successively with 50 % aqueous methanol and water, and recrystallized from a mixed solvent (about 400 ml) of ethyl acetate/hexane [2:1 (v/v)] to give the desired product (51.65 g), m.p. 212°–213 ° C.

EXAMPLES 2–22

Using the suitable starting materials, the compounds of the following Examples 2–22 are obtained in the same manner as in Example 1.

EXAMPLE 2

(2) Methyl 1-(4-fluorophenyl)-5-oxo-pyrrolidinecarboxylate

NMR (CDCl$_3$) δ ppm: 7.62–7.47 (m, 2H), 7.14–6.95 (m, 2H), 4.10–3.99 (m, 2H), 3.78 (s, 3H), 3.56–3.21 (m, 1H), 2.93–2.82 (m, 2H).

(3) 1-(4-Fluorophenyl)-4-hydroxymethyl-2-pyrrolidone

NMR (CDCl$_3$) δppm: 7.63–7.47 (m, 2H), 7.13–7.01 (m, 2H), 4.10–3.48 (m, 4H), 2.95–2.23 (m, 4H).

(4) Methyl 4-[1-(4-fluorophenyl)-2-pyrrolidon-4-yl]methoxybenzoate, m.p. 114°–116° C.

(5) 4-[1-(4-Fluorophenyl)-2-pyrrolidon-4-yl]methoxybenzoic acid, m.p. 230°–232° C.

EXAMPLE 3

(2) Methyl 1-(4-chlorophenyl)-5-oxo-3-pyrrolidinecarboxylate, m.p. 85°–87° C.

(3) 1-(4-Chlorophenyl)-4-hydroxymethyl-2-pyrrolidone

NMR(CDCl$_3$) δ ppm: 7.53 (d, 2H, J=9.0 Hz), 7.30 (d, 2H, J=9.0 Hz), 4.01 –3.52 (m, 4H), 2.78 –2.34 (m, 4H).

(4) Methyl 4-[1-(4-chlorophenyl)-2-pyrrolidon-4-yl]methoxybenzoate, m.p. 122°–124° C.

(5) 4-[1-(4-Chlorophenyl)-2-pyrrolidon-4-yl]-methoxybenzoic acid, m.p. 214°–215° C.

EXAMPLE 4

(2) Methyl 1-(3-chlorophenyl)-5-oxo-3-pyrrolidinecarboxylate

NMR (CDCl$_3$) δ ppm: 7.67 –7.07 (m, 4H), 4.11 –4.00 (m, 2H), 3.78 (s, 3H), 3.56 –3.20 (m, 1H), 2.95 –2.84 (m, 2H). (3) 1-(3-Chlorophenyl)-4-hydroxymethyl-2-pyrrolidone NMR (CDCl$_3$) δ ppm: 7.68 –7.04 (m, 4H), 4.02 –3.54 (m, 4H), 2.87 –2.24 (m, 4H).

(4) Methyl 4-[1-(3-chlorophenyl)-2-pyrrolidon-4-yl]methoxybenzoate, m.p. 90°–91° C.

(5) 4-[1-(3-Chlorophenyl)-2-pyrrolidon-4-yl]methoxybenzoic acid, m.p. 220°–223° C.

EXAMPLE 5

(2) Methyl 1-(2-chlorophenyl)-5-oxo-3-pyrrolidinecarboxylate

NMR (CDCl$_3$) δ ppm: 7.54 –7.23 (m, 4H), 4.03 –3.95 (m, 2H), 3.78 (s, 3H), 3.63 –3.29 (m, 1H), 2.92 –2.81 (m, 2H).

(3) 1-(2-Chlorophenyl)-4-hydroxymethyl-2-pyrrolidone

NMR (CDCl$_3$) δ ppm: 7.51 –7.20 (m, 4H), 3.93 –3.50 (m, 4H), 2.92 –2.18 (m, 4H).

(4) Methyl 4-[1-(2-chlorophenyl)-2-pyrrolidon-4-yl]methoxybenzoate

NMR (CDCl$_3$) δ ppm: 7.99 (d, 2H, J=8.8 Hz), 7.56–7.23 (m, 4H), 6.95 (d, 2H, J=8.8 Hz), 4.17 –3.66 (m, 7H), 3.30 –2.37 (m, 3H).

(5) 4-[1-(2-Chlorophenyl)-2-pyrrolidon-4-yl]-methoxybenzoic acid, m.p. 220°–223° C.

EXAMPLE 6

(2) Methyl 1-phenyl-5-oxo-3-pyrrolidinecarboxylate, m.p. 68°–69° C.

(3) 1-Phenyl-4-hydroxymethyl-2-pyrrolidone

NMR (CDCl$_3$) δ ppm: 7.63 –7.12 (m, 5H), 4.08 –3.49 (m, 4H), 2.94 –2.24 (m, 4H).

(4) Methyl 4-(1-phenyl-2-pyrrolidon-4-yl)methoxybenzoate

NMR (CDCl$_3$) δ ppm: 7.99 (d, 2H, J=8.8 Hz), 7.66–7.14 (m, 5H), 6.91 (d, 2H, J=8.8 Hz), 4.17 –3.74 (m, 7H), 3.17 –2.47 (m, 3H).

(5) 4-(1-Phenyl-2-pyrrolidon-4-yl)methoxybenzoic acid, m.p. 196°–199° C.

EXAMPLE 7

(1) 1-(4-n-Propylphenyl)-5-oxo-3-pyrrolidinecarboxylic acid, m.p. 129°–132° C.

(2) Methyl 1-(4-n-propylphenyl)-5-oxo-3-pyrrolidinecarboxylate

NMR (CDCl$_3$) δ ppm: 7.46 (d, 2H, J=8.6 Hz), 7.18 (d, 2H, J=8.6 Hz), 4.11 –4.01 (m, 2H), 3.77 (s, 3H), 3.54 –3.18 (m, 1H), 2.93 –2.82 (m, 2H), 2.57 (t, 2H, J=7.5 Hz), 1.84 –1.43 (m, 2H), 0.93 (t, 3H, J=7.0 Hz).

(3) 1-(4-n-Propylphenyl)-4-hydroxymethyl-2-pyrrolidone

NMR (CDCl$_3$) δ ppm: 7.47 (d, 2H, J=8.6 Hz), 7.17 (d, 2H, J=8.6 Hz), 4.04 –3.63 (m, 4H), 2.93 –2.10 (m, 6H), 1.83 –1.43 (m, 2H), 0.92 (t, 3H, J=7.2 Hz).

(4) Methyl 4-[1-(4-n-propylphenyl)-2-pyrrolidon-4-yl]methoxybenzoate, m.p. 97°–98° C.

(5) 4-[1-(4-n-Propylphenyl)-2-pyrrolidon-4-yl]methoxybenzoic acid, m.p. 193°–195° C.

EXAMPLE 8

(1) 1-(4-n-Butylphenyl)-5-oxo-3-pyrrolidinecarboxylic acid

NMR (DMSO-d$_6$) δ ppm: 7.52 (d, 2H, J=8.6 Hz), 7.18 (d, 2H, J=8.6 Hz), 4.16 –3.94 (m, 2H), 3.51 –3.15 (m, 1H), 2.77 –2.47 (m, 4H), 1.72 –1.11 (m, 4H), 0.89 (t, 3H, J=6.7 Hz).

(2) Methyl 1-(4-n-butylphenyl)-5-oxo-3-pyrrolidinecarboxylate

NMR (CDCl$_3$) δ ppm: 7.45 (d, 2H, J=8.6 Hz), 7.19 (d, 2H, J=8.6 Hz), 4.11 –4.00 (m, 2H), 3.77 (s, 3H), 3.54 –3.19 (m, 1H), 2.93 –2.82 (m, 2H), 2.59 (t, 3H, J=7.3 Hz), 1.75 –1.15 (m, 4H), 0.92 (t, 3H, J=6.3 Hz).

(3) 1-(4-n-Butylphenyl)-4-hydroxymethyl-2-pyrrolidone

NMR (CDCl$_3$) δ ppm: 7.46 (d, 2H, J=8.7 Hz), 7.16 (d, 2H, J=8.7 Hz), 4.04 –3.52 (m, 4H), 2.85 –2.21 (m, 6H), 1.74 –1.14 (m, 4H), 0.91 (t, 3H, J=6.8 Hz).

(4) Methyl 4-[1-(4-n-butylphenyl)-2-pyrrolidon-4-yl]methoxybenzoate, m.p. 82°–85° C.

(5) 4-[1-(4-n-Butylphenyl)-2-pyrrolidon-4-yl]methoxybenzoic acid, m.p. 186°–188° C.

EXAMPLE 9

(1) 1-(4-tert-Butylphenyl)-5-oxo-3-pyrrolidinecarboxylic acid, m.p. 208°–209° C.

(2) Methyl 1-(4-tert-butylphenyl)-5-oxo-3-pyrrolidinecarboxylate, m.p. 206°–209° C.

(3) 1-(4-tert-Butylphenyl)-4-hydroxymethyl-2-pyrrolidone

NMR (CDCl$_3$) δ ppm: 7.49 (d, 2H, J=9.2 Hz), 7.39 (d, 2H, J=9.2 Hz), 4.05 –3.53 (m, 4H), 2.93 –2.83 (m, 5H), 1.30 (s, 9H).

(4) Methyl 4-[1-(4-tert-butylphenyl)-2-pyrrolidon-4-yl]methoxybenzoate, m.p. 142°–144° C.

(5) 4-[1-(4-tert-Butylphenyl)-2-pyrrolidon-4yl]methoxybenzoic acid, m.p. 258°–260° C.

EXAMPLE 10

(1) 1-(4-n-Pentylphenyl)-5-oxo-3-pyrrolidinecarboxylic acid

NMR (DMSO-d$_6$) δ ppm: 7.52 (d, 2H, J=8.6 Hz), 7.18 (d, 2H, J=8.6 Hz), 4.16 –3.83 (m, 2H), 3.51 –3.17 (m, 1H), 2.77 –2.46 (m, 4H), 1.73 –1.13 (m, 6H), 0.85 (t, 3H, J=5.5 Hz).

(2) Methyl 1-(4-n-pentylphenyl)-5-oxo-3-pyrrolidinecarboxylate

NMR (CDCl$_3$) δ ppm: 7.45 (d, 2H, J=8.6 Hz), 7.18 (d, 2H, J=8.6 Hz), 4.10 –3.99 (m, 2H), 3.76 (s, 3H), 3.52 –3.18 (m, 1H), 2.92 –2.81 (m, 2H), 2.58 (t, 2H, J=7.3 Hz), 1.78 –1.16 (m, 6H), 0.88 (t, 3H, J=5.9 Hz).

(3) 1-(4-n-Pentylphenyl)-4-hydroxymethyl-2-pyrrolidone

NMR (CDCl$_3$) δ ppm: 7.47 (d, 2H, J=8.6 Hz), 7.17 (d, 2H, J=8.6 Hz), 4.05 –3.55 (m, 4H), 2.89 –2.32 (m, 5H), 2.12 (b, 1H), 1.77 –1.16 (m, 6H), 0.88 (t, 3H, J=5.5 Hz).

(4) Methyl 4-[1-(4-n-pentylphenyl)-2-pyrrolidon-4-yl]methoxybenzoate, m.p. 105°–108° C.

(5) 4-[1-(4-n-Pentylphenyl)-2-pyrrolidon-4-yl]methoxybenzoic acid, m.p. 190°–192° C.

EXAMPLE 11

(1) 1-(4-n-Hexylphenyl)-5-oxo-3-pyrrolidinecarboxylic acid

NMR (DMSO-d$_6$) δ ppm: 7.52 (d, 2H, J=8.6 Hz), 7.17 (d, 2H, J=8.6 Hz), 4.16 –3.83 (m, 2H), 3.51 –3.16 (m, 1H), 2.77 –2.46 (m, 4H), 1.71 –1.11 (m, 8H), 0.85 (b, 3H).

(2) Methyl 1-(4-n-hexylphenyl)-5-oxo-3-pyrrolidinecarboxylate

NMR (CDCl$_3$) δ ppm: 7.45 (d, 2H, J=8.6 Hz), 7.17 (d, 2H, J=8.6 Hz), 4.10 –3.99 (m, 2H), 3.76 (s, 3H), 3.55 –3.17 (m, 1H), 2.91 –2.81 (m, 2H), 2.58 (t, 2H, J=7.7 Hz), 1.77 –1.14 (m, 8H), 0.88 (b, 3H).

(3) 1-(4-n-Hexylphenyl)-4-hydroxymethyl-2-pyrrolidone

NMR (CDCl$_3$) δ ppm: 7.44 (d, 2H, J=8.7 Hz), 7.15 (d, 2H, J=8.7 Hz), 4.06 –3.53 (m, 4H), 3.07 (b, 1H), 2.84 –2.20 (m, 5H), 1.75 –1.17 (m, 8H), 0.88 (b, 3H).

(4) Methyl 4-[1-(4-n-hexylphenyl)-2-pyrrolidon-4-yl]methoxybenzoate, m.p. 119°–122° C.

(5) 4-[1-(4-n-Hexylphenyl)-2-pyrrolidon-4-yl]methoxybenzoic acid, m.p 191°–192° C.

EXAMPLE 12

(1) 1-(4-Cyclohexylphenyl)-5-oxo-3-pyrrolidinecarboxylic acid, m.p. 187°–191° C.

(2) Methyl 1-(4-cyclohexylphenyl)-5-oxo-3-pyrrolidinecarboxylate, m.p. 104°–106° C.

(3) 1-(4-Cyclohexylphenyl)-4-hydroxymethyl-2-pyrrolidone

NMR (CDCl$_3$) δ ppm: 7.47 (d, 2H, J=8.7 Hz), 7.20 (d, 2H, J=8.7 Hz), 4.04 –3.54 (m, 4H), 2.87 –2.24 (m, 5H), 1.87 –1.28 (m, 10H).

(4) Methyl 4-[1-(4-cyclohexylphenyl)-2-pyrrolidon-4-yl]methoxybenzoate, m.p. 136°–138° C.

(5) 4-[1-(4-Cyclohexylphenyl)-2-pyrrolidon-4-yl]methoxybenzoic acid, m.p. 241°–243° C.

EXAMPLE 13

(1) 1-(4-Methoxyphenyl)-5-oxo-3-pyrrolidinecarboxylic acid, m.p. 171°-172° C.

(2) Methyl 1-(4-methoxyphenyl)-5-oxo-3-pyrrolidinecarboxylate, m.p. 84°-86° C.

(3) 1-(4-Methoxyphenyl)-4-hydroxymethyl-2-pyrrolidone

NMR (CDCl$_3$) $\delta$ ppm: 7.45 (d, 2H, J=9.1 Hz), 6.89 (d, 2H, J=9.1 Hz), 4.08 -3.52 (m, 7H), 2.85 -2.19 (m, 4H)

(4) Methyl 4-[1-(4-methoxyphenyl)-2-pyrrolidon-4-yl]methoxybenzoate, m.p. 109°-111° C.

(5) 4-[1-(4-Methoxyphenyl)-2-pyrrolidon-4-yl]methoxybenzoic acid, m.p. 193°-195° C.

EXAMPLE 14

(1) 1-(4-n-Butoxyphenyl)-5-oxo-3-pyrrolidinecarboxylic acid, m.p. 125°-128° C.

(2) Methyl 1-(4-n-butoxyphenyl)-5-oxo-3-pyrrolidinecarboxylate, m.p. 69°-70° C.

(3) 1-(4-n-Butoxyphenyl)-4-hydroxymethyl-2-pyrrolidone

NMR (CDCl$_3$) $\delta$ ppm: 7.43 (d, 2H, J=9.0 Hz), 6.88 (d, 2H, J=9.0 Hz), 4.00 -3.62 (m, 6H), 2.91 -2.19 (m, 4H), 1.90 -1.27 (m, 4H), 0.96 (t, 3H, J=6.6 Hz).

(4) Methyl 4-[1-(4-n-butoxyphenyl)-2-pyrrolidon-4-methoxybenzoate, m.p. 108°-110° C.

(5) 4-[1-(4-n-Butoxyphenyl)-2-pyrrolidon-4-yl]methoxybenzoic acid, m.p. 187°-188° C.

EXAMPLE 15

(1) 1-[4-(4-Chlorophenoxy)phenyl]-5-oxo-3-pyrrolidinecarboxylic acid

NMR (DMSO-d$_6$) $\delta$ ppm: 7.67 (d, 2H, J=9.0 Hz), 7.40 (d, 2H, J=9.0 Hz), 7.10 -6.94 (m, 4H), 4.18 -3.86 (m, 2H), 3.52 -3.18 (m, 1H), 2.79 -2.68 (m, 2H).

(2) Methyl 1-[4-(4-chlorophenoxy)phenyl]-5-oxo-3-pyrrolidinecarboxylate

NMR (CDCl$_3$) $\delta$ ppm: 7.53 (d, 2H, J=9.0 Hz), 7.30 (d, 2H, J=9.0 Hz), 7.05 -6.86 (m, 4H), 4.12 -4.01 (m, 2H), 3.78 (s, 3H), 3.58 -3.22 (m, 1H), 2.95 -2.84 (m, 2H).

(3) 1-[4-(4-Chlorophenoxy)phenyl]-4-hydroxymethyl-2-pyrrolidone

NMR (CDCl$_3$) $\delta$ ppm: 7.55 (d, 2H, J=9.1 Hz), 7.25 (d, 2H, J=9.1 Hz), 7.01 (d, 2H, J=9.1 Hz), 6.92 (d, 2H, J=9.1 Hz), 4.06 -3.53 (m, 4H), 2.82 -2.35 (m, 3H), 1.96 (bs, 1H).

(4) Methyl 4-[1-[4-(4-chlorophenoxy)phenyl]-2-pyrrolidon- 4-yl]methoxybenzoate, m.p. 124°-127° C.

(5) 4-[1-[4-(4-Chlorophenoxy)phenyl]-2-pyrrolidon-4-yl]methoxybenzoic acid, m.p. 182°-183° C.

EXAMPLE 16

(1) 1-(3,4-Methylenedioxyphenyl)-5-oxo-3-pyrrolidinecarboxylic acid

NMR (DMSO-d$_6$) $\delta$ ppm: 7.36 (d, 1H, J=1.1 Hz), 7.03 -6.82 (m, 2H), 6.00 (s, 2H), 4.01 -3.91 (m, 2H), 3.49-3.15 (m, 1H), 2.66 (d, 2H, J=10.9 Hz).

(2) Methyl 1-(3,4-methylenedioxyphenyl)-5-oxo-3-pyrrolidinecarboxylate, m.p. 144°-146° C.

(3) 1-(3,4-Methylenedioxyphenyl)-4-hydroxymethyl-2-pyrrolidone

NMR (CDCl$_3$) $\delta$ ppm: 7.26 (d, 1H, J=1.8 Hz), 6.92-6.71 (m, 2H), 5.93 (s, 2H), 3.99 -3.51 (m, 4H), 2.85 -2.30 (m, 4H).

(4) Methyl 4-[1-(3,4-methylenedioxyphenyl)-2-pyrrolidon-4-yl]methoxybenzoate, m.p. 157°-159° C.

(5) 4-[1-(3,4-Methylenedioxyphenyl)-2-pyrrolidon-4-yl]methoxybenzoic acid, m.p. 235°-238° C.

EXAMPLE 17

(2) Methyl 1-(3,4-dichlorophenyl)-5-oxo-3-pyrrolidinecarboxylate

NMR (CDCl$_3$) $\delta$ ppm: 7.77 (d, 1H, J=1.8 Hz), 7.59-7.36 (m, 2H), 4.09 -3.99 (m, 2H), 3.79 (s, 3H), 3.55 -3.20 (m, 1H), 2.95 -2.84 (m, 2H).

(3) 1-(3,4-Dichlorophenyl)-4-hydroxymethyl-2-pyrrolidone

NMR (CDCl$_3$) $\delta$ ppm: 7.79 (d, 1H, J=2.2 Hz), 7.59-7.33 (m, 2H), 4.00 -3.47 (m, 4H), 2.94 -2.25 (m, 4H).

(4) Methyl 4-[1-(3,4-dichlorophenyl)-2-pyrrolidon-4-yl]methoxybenzoate, m.p. 124°-127° C.

(5) 4-[1-(3,4-Dichlorophenyl)-2-pyrrolidon-4-yl]methoxybenzoic acid, m.p. 239°-242° C.

EXAMPLE 18

(1) 1-(5-Chloro-2-methoxyphenyl)-5-oxo-3-pyrrolidinecarboxylic acid, m.p. 193°-195° C.

(2) Methyl 1-(5-chloro-2-methoxyphenyl)-5-oxo-3-pyrrolidinecarboxylate

NMR (CDCl$_3$) $\delta$ ppm: 7.28 -7.17 (m, 2H), 6.88 (d, 1H, J=9.5 Hz), 3.93 (d, 2H, J=7.3 Hz), 3.82 (s, 3H), 3.77 (s, 3H), 3.59 -3.22 (m, 1H), 2.87 -2.76 (m, 2H).

(3) 1-(5-Chloro-2-methoxyphenyl)-4-hydroxymethyl-2-pyrrolidone

NMR (CDCl$_3$) $\delta$ ppm: 7.31 -7.17 (m, 2H), 6.88 (d, 1H, J=9.7 Hz), 3.94 -3.49 (m, 7H), 2.84 -2.28 (m, 3H), 2.13 (b, 1H).

(4) Methyl 4-[1-(5-chloro-2-methoxyphenyl)-2-pyrrolidon-4-yl]methoxybenzoate

NMR (CDCl$_3$) $\delta$ ppm: 7.99 (d, 2H, J=9.0 Hz), 7.28-7.16 (m, 2H), 6.98 -6.80 (m, 3H), 4.13 -3.62 (m, 10H), 3.15 -2.32 (m, 3H).

(5) 4-[1-)5-Chloro-2-methoxyphenyl)-2-pyrrolidon-4-yl]methoxybenzoic acid, m.p. 172°-173° C.

EXAMPLE 19

(1) 1-(4-Chloro-2-methylphenyl)-5-oxo-3-pyrrolidinecarboxylic acid

NMR (DMSO-d$_6$) $\delta$ ppm: 7.36 (bs, 1H), 7.25 (bs, 2H), 4.03 -3.70 (m, 2H), 3.57 -3.25 (m, 1H), 2.72 -2.61 (m, 2H), 2.13 (s, 3H).

(2) Methyl 1-(4-chloro-2-methylphenyl)-5-oxo-3-pyrrolidinecarboxylate

NMR (CDCl$_3$) $\delta$ ppm: 7.26 -7.01 (m, 3H), 3.95 -3.85 (m, 2H), 3.78 (s, 3H), 3.59 -3.25 (m, 1H), 2.89 -2.80 (m, 2H), 2.21 (s, 3H).

(3) 1-(4-Chloro-2-methylphenyl)-4-hydroxymethyl-2-pyriolidone

NMR (CDCl$_3$) $\delta$ ppm: 7.24 -7.00 (m, 3H), 3.87 -3.45 (m, 4H), 2.84 -2.29 (m, 4H), 2.19 (s, 3H). (4) Methyl 4-[1-(4-chloro-2-methylphenyl)-2-pyrrolidon-4-yl]methoxybenzoate NMR (CDCl$_3$) $\delta$ ppm: 8.00 (d, 2H, J=9.0 Hz), 7.26-6.87 (m, 5H), 4.16 -3.58 (m, 7H), 3.22 -2.37 (m, 3H), 2.23 (s, 3H).

(5) 4-[1-(4-Chloro-2-methylphenyl)-2-pyrrolidon-4-yl]methoxybenzoic acid, m.p. 165°-167° C.

EXAMPLE 20

(1) 1-(3,5-Dimethylphenyl)-5-oxo-3-pyrrolidinecarboxylic acid, m.p. 172°-175° C.

(2) Methyl 1-(3,5-dimethylphenyl)-5-oxo-3-pyrrolidinecarboxylate

NMR (CDCl₃) δ ppm: 7.18 (bs, 2H), 6.81 (bs, 1H), 4.09 –3.98 (m, 2H), 3.76 (s, 3H), 3.53 –3.17 (m, 1H), 2.91 –2.80 (m, 2H), 2.31 (s, 6H).

(3) 1-(3,5-Dimethylphenyl)-4-hydroxymethyl-2-pyrrolidone

NMR (CDCl₃) δ ppm: 7.19 (bs, 2H), 6.79 (bs, 1H), 4.03 –3.52 (m, 4H), 2.85 –2.42 (m, 4H), 2.30 (s, 6H)

(4) Methyl 4-[1-(3,5-dimethylphenyl)-2-pyrrolidon-4-yl]methoxybenzoate, m.p. 147°–148° C.

(5) 4-[1-(3,5-Dimethylphenyl)-2-pyrrolidon-4-yl]methoxybenzoic acid, m.p. 215°–217° C.

EXAMPLE 21

(1) 1-(2,5-Dimethylphenyl)-5-oxo-3-pyrrolidinecarboxylic acid

NMR (DMSO-d₆) δ ppm: 7.25 –6.99 (m, 3H), 4.01–3.66 (m, 2H), 3.53 –3.21 (m, 1H), 2.70 –2.60 (m, 2H), 2.26 (s, 3H), 2.07 (s, 3H).

(2) Methyl 1-(2,5-dimethylphenyl)-5-oxo-3-pyrrolidinecarboxylate

NMR (CDCl₃) δ ppm: 7.21 –6.96 (m, 3H), 3.96 –3.87 (m, 2H), 3.78 (s, 3H), 3.66 –3.25 (m, 1H), 2.91 –2.81 (m, 2H), 2.31 (s, 3H), 2.18 (s, 3H).

(3) 1-(2,5-Dimethylphenyl)-4-hydroxymethyl-2-pyrrolidone

NMR (CDCl₃) δ ppm: 7.19 –6.94 (m, 3H), 3.90 –3.46 (m, 4H), 2.89 –1.92 (m, 10H).

(4) Methyl 4-[1-(2,5-dimethylphenyl)-2-pyrrolidon-4-yl]methoxybenzoate

NMR (CDCl₃) δ ppm: 8.01 (d, 2H, J=9.0 Hz), 7.22–6.88 (m, 5H), 4.15 –3.58 (m, 7H), 3.20 –2.55 (m, 3H), 2.30 (s, 3H), 2.20 (s, 3H).

(5) 4-[1-(2,5-Dimethylphenyl)-2-pyrrolidon-4-yl]methoxybenzoic acid, m.p. 151°–154° C.

EXAMPLE 22

(1) 1-(2,4-Dimethylphenyl)-5-oxo-3-pyrrolidinecarboxylic acid

NMR (CDCl₃) δ ppm: 7.07 (bs, 1H), 7.02 (bs, 2H), 3.95 –3.86 (m, 2H), 3.56 –3.24 (m, 1H), 2.95 –2.86 (m, 2H), 2.30 (s, 3H), 2.18 (s, 3H).

(2) Methyl 1-(2,4-dimethylphenyl)-5-oxo-3-pyrrolidinecarboxylate

NMR (CDCl₃) δ ppm: 7.08 (bs, 1H), 7.03 (bs, 2H), 3.95 –3.86 (m, 2H), 3.78 (s, 3H), 3.57 –3.23 (m, 1H), 2.90 –2.80 (m, 2H), 2.31 (s, 3H), 2.19 (s, 3H).

(3) 1-(2,4-Dimethylphenyl)-4-hydroxymethyl-2-pyrrolidone

NMR (CDCl₃) δ ppm: 7.06 (bs, 1H), 7.01 (bs, 2H), 3.89 –3.44 (m, 4H), 2.76 –2.18 (m, 10H).

(4) Methyl 4-[1-(2,4-dimethylphenyl)-2-pyrrolidon-4-yl] methoxybenzoate

NMR (CDCl₃) δ ppm: 7.99 (d, 2H, J=9.0 Hz), 7.07–6.87 (m, 5H), 4.14–3.56 (m, 7H), 3.17–2.54 (m, 3H), 2.30 (s, 3H), 2.21 (s, 3H).

(5) 4-[1-(2,4-Dimethylphenyl)-2-pyrrolidon-4-yl]methoxybenzoic acid, m.p. 139°–142° C.

EXAMPLE 23

(1) 1-(4-Ethylphenyl)-5-oxo-3-pyrrolidinecarboxylic acid is obtained in the same manner as in Example 1–(1), m.p. 144°–146° C.

(2) 1-(4-Ethylphenyl)-4-hydroxymethyl-2-pyrrolidone 1-(4-Ethylphenyl)-5-oxo-3-pyrrolidinecarboxylic acid (5.00 g) is suspended in carbon tetrachloride (15 ml) and thereto is added thionyl chloride (2.32 ml). The reaction mixture is heated with stirring under refluxing for 1 hour and concentrated under reduced pressure. The residue is dissolved in tetrahydrofuran (25 ml) and thereto is added dropwise a solution of sodium boron hydride (1.61 g) in dimethylformamide (about 16 ml) under ice-cooling. The mixture is further stirred for 1 hour. Methanol (13 ml) and conc. hydrochloric acid (1.87 ml) are successively added dropwise into the reaction mixture and the mixture is concentrated under reduced pressure. Ethyl acetate (120 ml) is added to the residue and the mixture is washed with water three times, dried over anhydrous magnesium sulfate, and then concentrated again under reduced pressure. To this residue is added a mixed solvent (about 50 ml) of ethyl acetate/hexane [1:20 (v/v)]. The mixture is allowed to stand and the precipitated crystal is collected by filtration to give the desired product (3.81 g).

NMR (CDCl₃) δ ppm: 7.46 (d, 2H, J=8.7 Hz), 7.18 (d, 2H, J=8.7 Hz), 4.02–3.49 (m, 4H), 3.08–2.20 (m, 6H), 1.21 (t, 3H, J=7.5 Hz).

(3) Methyl 4-[1-(4-ethylphenyl)-2-pyrrolidon-4-yl]methoxybenzoate is obtained in the same manner as in Example 1–(4), m.p. 87°–88° C.

(4) 4-[1-(4-Ethylphenyl)-2-pyrrolidon-4-yl]methoxybenzoic acid is obtained in the same manner as in Example 1–(5), m.p. 195°–197° C.

EXAMPLES 24–26

Using the suitable starting materials, the compounds of the following Examples 24–26 are obtained in the same manner as in Example 23.

EXAMPLE 24

(2) 1-(4-Bromophenyl)-4-hydroxymethyl-2-pyrrolidone

NMR (CDCl₃) δ ppm: 7.46 (bs, 4H), 3.99–3.50 (m, 4H), 3.24 (b, 1H), 2.91–2.33 (m, 3H).

(3) Methyl 4-[1-(4-bromophenyl)-2-pyrrolidon-4-yl]methoxybenzoate, m.p. 130°–133° C.

(4) 4-[1-(4-Bromophenyl)-2-pyrrolidon-4-yl]methoxybenzoic acid, m.p. 216°–220° C.

EXAMPLE 25

(1) 1-(4-Isopropylphenyl)-5-oxo-3-pyrrolidinecarboxylic acid, m.p. 166°–168° C.

(2) 1-(4-Isopropylphenyl)-4-hydroxymethyl-2-pyrrolidone

NMR (CDCl₃) δ ppm: 7.47 (d, 2H, J=8.6 Hz), 7.21 (d, 2H, J=8.6 Hz), 4.09–3.52 (m, 4H), 3.09–2.17 (m, 5H), 1.23 (d, 6H, J=7.0 Hz).

(3) Methyl 4-[1-(4-isopropylphenyl)-2-pyrrolidon-4-yl]methoxybenzoate, m.p. 104°–105° C.

(4) 4-[1-(4-Isopropylphenyl)-2-pyrrolidon-4-yl]methoxybenzoic acid, m.p. 209°–210° C.

EXAMPLE 26

(1) 1-(4-Ethoxycarbonylphenyl)-5-oxo-3-pyrrolidinecarboxylic acid, m.p. 182°–186° C.

(2) 1-(4-Ethoxycarbonylphenyl)-4-hydroxymethyl-2-pyrrolidone

NMR (CDCl₃) δ ppm: 8.01 (d, 2H, J=9.1 Hz), 7.72 (d, 2H, J=9.1 Hz), 4.36 (q, 2H, J=7.1 Hz), 4.10–3.58 (m, 4H), 2.83–2.39 (m, 3H), 2.09 (b, 1H), 1.38 (t, 3H, J=7.1 Hz)

(3) Methyl 4-[1-(4-ethoxycarbonylphenyl)-2-pyrrolidon-4-yl]methoxybenzoate. m.p. 121°–123° C.

(4) 4-[1-(4-Carboxyphenyl)-2-pyrrolidon-4-yl]methoxybenzoic acid, m.p. >300° C.

NMR (DMSO-d6) δ ppm: 8.02-7.75 (m, 6H), 7.04 (d, 2H, J=8.8 Hz), 4.19-3.71 (m, 4H), 3.13-2.31 (m, 3H).

EXAMPLE 27

(1) 1-(4-Hydroxyphenyl)-5-oxo-3-pyrrolidinecarboxylic acid is obtained in the same manner as in Example 1—(1), m.p. 201°-204° C.

(2) Methyl 1-(4-hydroxyphenyl)-5-oxo-3-pyrrolidinecarboxylate is obtained in the same manner as in Example 1-(2).

NMR (CDCl$_3$) δ ppm: 7.24 (d, 2H, J=9.0 Hz), 6.77 (d, 2H, J=9.0 Hz), 4.06-3.96 (m, 2H), 3.76 (s, 3H), 3.55-3.20 (m, 1H), 2.93-2.82 (m, 2H).

(3) Methyl 1-(4-ethoxyphenyl)-5-oxo-3-pyrrolidinecarboxylate

Methyl 1-(4-hydroxyphenyl)-5-oxo-3-pyrrolidinecarboxylate (3.00 g) is dissolved in dimethylformamide (30 ml) and thereto are added potassium carbonate (4.40 g) and ethyl iodide (2.56 ml). The mixture is heated with stirring at 80° C. for 22 hours. The reaction solution is concentrated under reduced pressure and the resulting residue is neutralized by adding thereto water and 1N hydrochloric acid. The precipitated crystal is collected by filtration and washed with water to give the desired product (3.07 g), m.p. 67°-69° C.

(4) 1-(4-Ethoxyphenyl)-4-hydroxymethyl-2-pyrrolidone is obtained in the same manner as in Example 1-(3).

NMR (CDCl$_3$) δ ppm: 7.43 (d, 2H, J=9.1 Hz), 6.88 (d, 2H, J=9.1 Hz), 4.13-3.50 (m, 6H), 2.95-2.18 (m, 4H), 1.39 (t, 3H, J=7.0 Hz).

(5) Methyl 4-[1-(4-ethoxyphenyl)-2-pyrrolidon-4-yl]methoxybenzoate is obtained in the same manner as in Example 1-(4), m.p. 117°-118° C.

(6) 4-[1-(4-Ethoxyphenyl)-2-pyrrolidon-4-yl]methoxybenzoic acid is obtained in the same manner as in Example 1-(5), m.p. 218°-220° C.

EXAMPLES 28-33

Using the suitable starting materials, the compounds of the following Examples 28-33 are obtained in the same manner as in Example 27-(3)~(6).

EXAMPLE 28

(1) Methyl-(4-n-propoxyphenyl)-5-oxo-3-pyrrolidinecarboxylate

NMR (CDCl$_3$) δ ppm: 7.43 (d, 2H, J=9.1 Hz), 6.90 (d, 2H, J=9.1 Hz), 4.08-3.83 (m, 4H), 3.77 (s, 3H), 3.54-3.19 (m, 1H), 2.91-2.80 (m, 2H), 2.00-1.60 (m, 2H), 1.02 (t, 3H, J=7.1 Hz).

(2) 1-(4-n-Propoxyphenyl)-4-hydroxymethyl-2-pyrrolidone

NMR (CDCl$_3$) δ ppm: 7.43 (d, 2H, J=9.0 Hz), 6.88 (d, 2H, J=9.0 Hz), 3.96-3.61 (m, 6H), 2.99-2.19 (m, 4H), 1.99-1.60 (m, 2H), 1.02 (t, 3H, J=7.3 Hz).

(3) Methyl 4-[1-(4-n-propoxyphenyl)-2-pyrrolidon-4-yl]methoxybenzoate, m.p. 104°-105° C.

(4) 4-[1-(4-n-Propoxyphenyl)-2-pyrrolidon-4-yl]methoxybenzoic acid, m.p. 197°-198° C.

EXAMPLE 29

(1) Methyl 1-(4-isopropoxyphenyl)-5-oxo-3-pyrrolidinecarboxylate

NMR (CDCl$_3$) δ ppm: 7.42 (d, 2H, J=9.1 Hz), 6.89 (d, 2H, J=9.1 Hz), 4.64-4.37 (m, 1H), 4.08-3.97 (m, 2H), 3.77 (s, 3H), 3.52-3.18 (m, 1H), 2.91-2.81 (m, 2H), 1.32 (d, 6H, J=5.9 Hz).

(2) 1-(4-Isopropoxyphenyl)-4-hydroxymethyl-2-pyrrolidone

NMR (CDCl$_3$) δ ppm: 7.44 (d, 2H, J=9.1 Hz), 6.88 (d, 2H, J=9.1 Hz), 4.64-4.37 (m, 1H), 4.01-3.53 (m, 4H), 2.94-1.98 (m, 4H), 1.31 (d, 6H, J=6.2 Hz).

(3) Methyl 4-[1-(4-isopoxyphenyl)-2-pyrrolidon-4-yl]methoxybenzoate, m.p. 99°-100° C.

(4) 4-[1-(4-Isopropoxyphenyl)-2-pyrrolidone-4-yl]methoxybenzoic acid, m.p. 186°-188° C.

EXAMPLE 30

(1) Methyl 1-(4-benzyloxyphenyl)-5-oxo-3-pyrrolidinecarboxylate

NMR (CDCl$_3$) δ ppm: 7.51-7.25 (m, 7H), 6.97 (d, 2H, J=9.0 Hz), 5.04 (s, 2H), 4.07-3.96 (m, 2H), 3.76 (s, 3H), 3.51-3.18 (m, 1H), 2.90-2.80 (m, 2H).

(2) 1-(4-Benzyloxyphenyl)-4-hydroxymethyl-2-pyrrolidone

NMR (CDCl$_3$) δ ppm: 7.51-7.26 (m, 7H), 6.95 (d, 2H, J=9.2 Hz), 5.02 (s, 2H), 3.98-3.47 (m, 4H), 2.88-2.16 (m, 4H).

(3) Methyl 4-[1-(4-benzyloxyphenyl)-2-pyrrolidon-4-yl]methoxybenzoate

NMR (CDCl$_3$) δ ppm: 7.99 (d, 2H, J=8.8 Hz), 7.55-7.37 (m, 7H), 7.01-6.86 (m, 4H), 5.05 (s, 2H), 4.09-3.49 (m, 7H); 3.13-2.34 (m, 3H).

(4) 4-[1-(4-Benzyloxyphenyl)-2-pyrrolidon-4-yl]methoxybenzoic acid, m.p. 208°-211° C.

EXAMPLE 31

(1) Methyl 1-[4-(4-chlorobenzyloxy)phenyl]-5-oxo-3-pyrrolidinecarboxylate

NMR (CDCl$_3$) δ ppm: 7.45 (d, 2H, J=9.1 Hz), 7.34 (s, 4H), 6.95 (d, 2H, J=9.1 Hz), 5.01 (s, 2H), 4.08-3.97 (m, 2H), 3.77 (s, 3H), 3.53-3.18 (m, 1H), 2.91-2.81 (m, 2H).

(2) 1-[4-(4-Chlorobenzyloxy)phenyl]-4-hydroxymethyl-2-pyrrolidone

NMR (CDCl$_3$) δ ppm: 7.54-7.26 (m, 6H), 6.94 (d, 2H, J=9.0 Hz), 5.01 (s, 2H), 4.03-3.56 (m, 4H), 2.93-2.32 (m, 3H), 2.09 (b, 1H).

(3) Methyl 4-[1-[4-(4-chlorobenzyloxy)phenyl]-2-pyrrolidon-4-yl]methoxybenzoate

NMR (CDCl$_3$) δ ppm: 7.99 (d, 2H, J=8.8 Hz, 7.51 (d, 2H, J=9.0 Hz), 7.33 (s, 4H), 6.99-6.86 (m, 4H), 5.00 (s, 2H), 4.09-3.54 (m, 7H), 3.12-2.31 (m, 3H)

(4) 4-[1-[4-(4-Chlorobenzyloxy)phenyl]-2-pyrrolidon-4-yl]methoxybenzoic acid, m.p. 214°-217° C.

EXAMPLE 32

(1) Methyl 1-[4-(4-isopropylbenzyloxy)phenyl]-5-oxo-3-pyrrolidinecarboxylate

NMR (CDCl$_3$) δ ppm: 7.51-7.17 (m, 6H), 6.98 (d, 2H, J=9.2 Hz), 5.01 (s, 2H), 4.08-3.97 (m, 2H), 3.77 (s, 3H), 3.52-3.08 (m, 1H), 2.91-2.81 (m, 2H), 1.25 (d, 6H, J=7.0 Hz).

(2) 1-[4-(4-Isopropylbenzyloxy)phenyl]-4-hydroxymethyl-2-pyrrolidone

NMR (CDCl$_3$) δ ppm: 7.52-7.18 (m, 6H), 6.96 (d, 2H, J=9.2 Hz), 4.99 (s, 2H), 4.00-3.52 (m, 4H), 3.18-2.40 (m, 4H), 2.29 (b, 1H), 1.24 (d, 6H, J=6.8 Hz).

(3) Methyl 4-[1-[4-(4-isopropylbenzyloxy)phenyl]-2-pyrrolidon-4-yl]methoxybenzoate NMR (CDCl$_3$) δ ppm: 7.99 (d, 2H, J=9.0 Hz), 7.48 (d, 2H, J=9.2 Hz), 7.41-7.18 (m, 4H), 7.02-6.86 (m, 4H), 5.01 (s, 2H), 4.10-3.69 (m, 7H), 3.18-2.43 (m, 3H), 1.25 (d, 6H, J=7.0 Hz).

(4) 4-[1-[4-(4-Isopropylbenzyloxy)phenyl]-2-pyrrolidon-4-yl]methoxybenzoic acid, m.p. 208°-211° C.

EXAMPLE 33

(1) Methyl 1-[4-(4-tert-butylbenzyloxy)phenyl]-5-oxo-3-pyrrolidinecarboxylate

NMR (CDCl$_3$) δ ppm: 7.51-7.33 (m, 6H), 6.98 (d, 2H, J=9.2 Hz), 5.01 (s, 2H), 4.08-3.97 (m, 2H), 3.76 (s, 3H), 3.54-3.18 (m, 1H), 2.91-2.80 (m, 2H), 1.32 (s, 9H).

(2) 1-[4-(4-tert-Butylbenzyloxy)phenyl]-4-hydroxymethyl-2-pyrrolidone

NMR (CDCl$_3$) δ ppm: 7.53-7.37 (m, 6H), 6.97 (d, 2H, J=9.2 Hz), 5.00 (s, 2H), 4.01-3.53 (m, 4H), 2.78-2.31 (m, 3H), 2.08 (b, 1H), 1.32 (s, 9H).

(3) Methyl 4-[1-[4-(4-tert-butylbenzyloxy)phenyl]-2-pyrrolidon-4-yl]methoxybenzoate, m.p. 136°-139° C.

(4) 4-[1-[4-(4-tert-Butylbenzyloxy)phenyl]-2-pyrrolidon-4-yl]methoxybenzoic acid, m.p. 280° C.(decomposed)

NMR (DMSO-d6) δ ppm: 7.87 (d, 2H, J=8.6 Hz), 7.54 (d, 2H, J=9.0 Hz), 7.37 (s, 4H), 7.04-6.86 (m, 4H), 5.04 (s, 2H), 4.11-3.60 (m, 4H), 3.05-2.25 (m, 3H), 1.28 (s, 9H)

EXAMPLE 34

(1) Methyl 4-[1-(4-hydroxyphenyl)-2-pyrrolidon-4-yl]methoxybenzoate

Methyl 4-[1-(4-benzyloxyphenyl)-2-pyrrolidon-4-yl]methoxybenzoate (2.00 g) is dissolved in a mixed solvent of chloroform (50 ml) and methanol (20 ml), and thereto is added 10% palladium-carbon (0.2 g). The mixture is stirred at room temperature at atmospheric pressure under hydrogen atmosphere for 22 hours. The catalyst is removed by filtration and the filtrate is concentrated under reduced pressure. The residue is crystallized from 50% aqueous methanol (about 20 ml) to give the desired product (1.50 g), m.p. 141°-144° C.

(2) 4-[1-(4-Hydroxyphenyl)-2-pyrrolidon-4-yl]methoxybenzoic acid is obtained in the same manner as in Example 1-(5), m.p. 246°-249° C.

Using the suitable starting materials, the compounds of the following Examples 35-42 are obtained in the same manner as in Example 1.

EXAMPLE 35

(1) Methyl 4-[1-(4-chlorophenyl)-2-pyrrolidon-4-yl]methoxycinnamate, m.p. 137°-138° C.

(2) 4-[1-(4-Chlorophenyl)-2-pyrrolidon-4-yl]methoxycinnamic acid, m.p. 206°-207° C.

EXAMPLE 36

(1) Methyl 4-[1-(4-chlorophenyl)-2-pyrrolidon-4-yl]methoxy-α-methylcinnamate, m.p. 156°-158° C.

(2) 4-[1-(4-Chlorophenyl)-2-pyrrolidon-4-yl]methoxy-α-methylcinnamic acid, m.p. 193°-194° C.

EXAMPLE 37

(1) Methyl 3-[4-[1-(4-chlorophenyl)-2-pyrrolidon-4-yl]methoxy]phenylpropionate, m.p. 113°-115° C.

(2) 3-[4-[1-(4-Chlorophenyl)-2-pyrrolidon-4-yl]methoxy]phenylpropionic acid, m.p. 122°-123° C.

EXAMPLE 38

(1) Methyl 3-[4-[1-(4-chlorophenyl)-2-pyrrolidon-4-yl] methoxy]phenyl-2-methylpropionate NMR (CDCl$_3$) δ ppm: 7.59 (d, 2H, J=9.23 Hz), 7.31 (d, 2H, J=9.45 Hz), 7.08 (d, 2H, J=8.79 Hz), 6.80 (d, 2H, J=8.79 Hz), 4.03-3.81 (m, 4H), 3.63 (s, 3H), 3.00-2.46 (m, 6H), 1.13 (d, 3H, J=6.6 Hz).

(2) 3-[4-[1-(4-Chlorophenyl)-2-pyrrolidon-4-yl]methoxy]phenyl-2-methylpropionic acid, m.p. 95°-97° C.

EXAMPLE 39

(1) Methyl 2-[1-(4-chlorophenyl)-2-pyrrolidon-4-yl]methoxybenzoate

NMR (CDCl$_3$) δ ppm: 7.84-7.75 (m, 1H), 7.61 (d, 2H, J=9.23 Hz), 7.36-7.26 (m, 3H), 7.09-6.91 (m, 2H), 4.14-3.94 (m, 4H), 3.83 (s, 3H), 3.10-2.63 (m, 3H).

(2) 2-[1-(4-Chlorophenyl)-2-pyrrolidon-4-yl]methoxybenzoic acid, m.p. 155°-156° C.

EXAMPLE 40

(4) Methyl 3-[1-(4-chlorophenyl)-2-pyrrolidon-4-yl]methoxybenzoate

NMR (CDCl$_3$) δ ppm: 7.71-7.04 (m, 8H), 4.12-3.57 (m, 7H), 3.14-2.36 (m, 3H)

(5) 3-[1-(4-Chlorophenyl)-2-pyrrolidon-4-yl]-methoxybenzoic acid, m.p. 156°-158° C.

EXAMPLE 41

(1) 1-(4-Chlorobenzyl)-5-oxo-3-pyrrolidinecarboxylic acid, m.p. 148°-150° C.

(2) Methyl 1-(4-chlorobenzyl)-5-oxo-3-pyrrolidinecarboxylic

NMR (CDCl$_3$) δ ppm: 7.37-7.11 (m, 4H), 4.42 (s, 2H), 3.71 (s, 3H), 3.51-3.06 (m, 3H), 2.77-2.67 (m, 2H).

(3) 1-(4-Chlorobenzyl)-4-hydroxymethyl-2-pyrrolidone

NMR (CDCl$_3$) δ ppm: 7.36-7.11 (m, 4H), 4.40 (s, 2H), 3.62-3.01 (m, 4H), 2.77-1.67 (m, 4H).

(4) Methyl 4-[1-(4-chlorobenzyl)-2-pyrrolidon-4-methoxybenzoate

NMR (CDCl$_3$) δ ppm: 7.96 (d, 2H, J=9.0 Hz), 7.36-7.12 (m, 4H), 6.83 (d, 2H, J=9.0 Hz), 4.43 (s, 2H), 3.99-3.88 (m, 5H), 3.60-3.11 (m, 2H), 2.96-2.24 (m, 3H).

(5) 4-[1-(4-Chlorobenzyl)-2-pyrrolidon-4-yl]methoxybenzoic acid, m.p. 180°-183° C.

EXAMPLE 42

(1) 1-(3,5-Di-tert-butyl-4-hydroxyphenyl)-5-oxo-3-pyrrolidinecarboxylic acid

NMR (DMSO-d6) δ ppm: 7.28 (s, 2H), 6.88 (s, 1H), 4.00-3.91 (m, 2H), 3.54-3.19 (m, 1H), 2.71-2.62 (m, 2H), 1.37 (s, 18H).

(2) Methyl 1-(3,5-di-tert-butyl-4-hydroxyphenyl)-5-oxo-3-pyrrolidinecarboxylate

NMR (CDCl$_3$) δ ppm: 7.28 (s, 2H), 5.15 (s, 1H), 4.08-3.97 (m, 2H), 3.77 (s, 3H), 3.53-3.18 (m, 1H), 2.90-2.80 (m, 2H), 1.44 (s, 18H).

(3) 1-(3,5-Di-tert-butyl-4-hydroxyphenyl)-4-hydroxymethyl- 2-pyrrolidone

NMR (CDCl$_3$) δ ppm: 7.31 (s, 2H), 5.15 (s, 1H), 4.02-3.50 (m, 4H), 2.77-2.30 (m, 4H), 1.43 (s, 18H).

(4) Methyl 4-[1-(3,5-di-tert-butyl-4-hydroxyphenyl)-2-pyrrolidon-4-yl]methoxybenzoate NMR (CDCl$_3$) δ ppm: 7.98 (d, 2H, J=8.9 Hz), 7.33 (s, 2H), 6.92 (d, 2H, J=8.9 Hz), 5.15 (s, 1H), 4.12-3.62 (m, 7H), 3.06-2.43 (m, 3H), 1.44 (s, 18H).

(5) 4-[1-(3,5-Di-tert-butyl-4-hydroxyphenyl)-2-pyrrolidon-4-yl]methoxybenzoic acid, m.p. 214°-217° C. (decomposed)

Using the suitable starting materials, the compounds of the following Example 43 are obtained in the same manner as in Example 23.

EXAMPLE 43

(1) 1-(4-Chlorophenyl)-6-oxo-3-piperidinecarboxylic acid, m.p. 184°–187° C.

(2) 1-(4-Chlorophenyl)-5-hydroxymethyl-2-piperidone

NMR (CDCl₃) δ ppm: 7.40–7.13 (m, 4H), 3.81–3.36 (m, 4H), 2.94–1.48 (m, 6H).

(3) Methyl 4-[1-(4-chlorophenyl)-2-piperidon-5-yl]methoxybenzoate, m.p. 148°–150° C.

(4) 4-[1-(4-Chlorophenyl)-2-piperidon-5-yl]methoxybenzoic acid, m.p. 195°–197° C.

EXAMPLE 44

(1) 1-(4-Chlorophenyl)-4-cyanomethyl-2-pyrrolidone 1-(4-Chlorophenyl)-4-hydroxymethyl-2-pyrrolidone (6.00 g) is dissolved in methylene chloride (60 ml) and the mixture is cooled with ice. Thereto are added dropwise methanesulfonyl chloride (2.88 ml) and triethylamine (7.36 ml) severally and the mixture is stirred at room temperature for 26 hours. The reaction mixture is concentrated under reduced pressure and water is added to the residue. The precipitate is crushed, collected by filtration, washed with water and n-hexane and dried to give a mesylate compound (8.03 g) as powder.

Subsequently, this mesylate compound is dissolved in DMF (40 ml) and thereto is added sodium cyanide (1.56 g) and the mixture is heated with stirring at 100° C. for 22 hours. After cooling, the reaction mixture is diluted with ethyl acetate (100 ml), washed with water three times and concentrated under reduced pressure. To the residue is added about 20% aqueous methanol (30 ml) and the resulting crystal is collected by filtration to give the desired product (5.20 g), m.p. 92°–94° C.

(2) Methyl 1-(4-chlorophenyl)-5-oxopyrrolidin-3-ylacetic acid 1-(4-Chlorophenyl)-4-cyanomethyl-2-pyrrolidone (5.00 g) and sodium hydroxide (2.56 g) are refluxed in a mixed solvent of ethanol (2.5 ml) and water (15 ml) for 8 hours. The reaction mixture is concentrated under reduced pressure and the residue is dissolved again in water. The aqueous solution is washed with diethyl ether, neutralized with conc. hydrochloric acid and extracted with methylene chloride (80 ml) twice. The extract is dried over magnesium sulfate and concentrated under reduced pressure to give an oily product.

This oily product is dissolved in absolute methanol (100 ml) and thereto is added sulfuric acid (0.11 ml) and the mixture is refluxed for 15 hours. The reaction mixture is concentrated under reduced pressure and to the residue is added ethyl acetate (100 ml), washed successively with aqueous sodium hydrogen carbonate solution and water. The mixture is dried over magnesium sulfate and concentrated under reduced pressure to give the desired product (5.36 g), m.p. 63°–67° C.

(3) 1-(4-Chlorophenyl)-4-(2-hydroxyethyl)-2-pyrrolidone

Using methyl 1-(4-chlorophenyl)-5-oxopyrrolidin-3-ylacetate (5.20 g) as a starting material, the desired product (4.24 g) is obtained in the same manner as in Example 1–(3) as oil.

NMR (CDCl₃) δ ppm: 7.53 (d, 2H, J=9.0 Hz), 7.31 (d, 2H, J=9.0 Hz), 4.05–3.45 (m, 4H), 2.91–2.15 (m, 3H), 1.89–1.69 (m, 3H).

(4) Methyl 4-[2-[1-(4-chlorophenyl)-2-pyrrolidon-4-yl]ethoxy]benzoate

Using 1-(4-chlorophenyl)-4-(2-hydroxyethyl)-2-pyrrolidone (4.23 g) as a starting material, the desired product (5.44 g) is obtained in the same manner as in Example 1–(4), m.p. 126°–128° C.

(5) 4-[2-[1-(4-Chlorophenyl)-2-pyrrolidon-4-yl]ethoxy]benzoic acid

Using methyl 4-[2-[1-(4-chlorophenyl)-2-pyrrolidon-4-yl]ehtoxy]benzoate (5.20 g) as a starting material, the desired product (5.13 g) is obtained in the same manner as in Example 1–(5), m.p. 228°–229° C.

EXAMPLE 45

(1) Ethyl 1-(3,4-methylenedioxyphenoxyacetyl)-piperidine-4-carboxylate 3,4-Methylenedioxyphenoxyacetic acid (3.50 g) is suspended in carbon tetrachloride (8 ml) and thereto is added thionyl chloride (1.93 ml) and the mixture is refluxed for 1.5 hour. The reaction mixture is concentrated under reduced pressure to give an acid chloride. Ethyl isonipecotate (2.72 ml) and triethylamine (7.41 ml) are dissolved in THF (30 ml) and thereto is added above acid chloride under ice-cooling and the mixture is stirred at room temperature for 19 hours. The reaction mixture is concentrated under reduced pressure and after adding water and ethyl acetate to the residue, the mixture is separated into layers. The organic layer is washed with water three times, dried over magnesium sulfate and concentrated under reduced pressure to give the desired product (6.58 g) as oil.

NMR (CDCl₃) δ ppm: 6.68 (d, 1H, J=8.6 Hz), 6.53 (d, 1H, J=2.2 Hz), 6.42–6.29 (m, 1H), 5.91 (s, 2H), 4.60 (s, 2H), 4.42–3.85 (m, 4H), 3.31–2.77 (m, 2H), 2.67–2.40 (m, 1H), 2.07–1.52 (m, 4H), 1.25 (t, 3H, J=7.1 Hz).

(2) 1-[2-(3,4-Methylenedioxyphenoxy)ethyl]-4-hydroxymethylpiperidine

Lithium aluminum hydride (1.81 g) is suspended in THF (60 ml) under ice-cooling and thereto is added dropwise a solution of ethyl 1-(3,4-methylenedioxyphenoxyacetyl)-piperidine-4-carboxylate (4.00 g) in THF (20 ml). The mixture is stirred at room temperature for 30 minutes, and further stirred under refluxing for 14 hours. To the reaction mixture are added ethyl acetate and a small amount of 1N aqueous sodium hydroxide solution to decompose the excess reducing agent. The mixture is filtered and the filtrate is concentrated under reduced pressure to give the desired product (3.25 g).

NMR (CDCl₃) δ ppm: 6.69 (d, 1H, J=8.6 Hz), 6.50 (d, 1H, J=2.4 Hz), 6.38–6.26 (m, 1H), 5.90 (s, 2H), 4.03 (t, 2H, J=5.9 Hz), 3.49 (d, 2H, J=5.1 Hz), 3.09–2.97 (m, 2H), 2.76 (t, 2H, J=5.9 Hz), 2.27–2.03 (m, 2H), 184–1.37 (m, 6H).

(3) Methyl 4-[1-[2-(3,4-methylenedioxyphenoxy)ethyl]piperidin-4-yl]methoxybenzoate 1-[2-(3,4-Methylenedioxyphenoxy)ethyl]-4-hydroxymethylpiperidine (3.25 g) is dissolved in methylene chloride (35 ml) and cooled with ice. Thereto are added methanesulfonyl chloride (1.08 ml) and triethylamine (4.84 ml) and the mixture is stirred at room temperature for 14 hours. The mixture is concentrated under reduced pressure, and the residue is dissolved in DMF (15 ml). To the mixture are added methyl p-hydroxybenzoate (1.76 g) and potassium carbonate (3.20 g) and the mixture is heated with stirring at 100° C. for 2 days. After cooling, the reaction mixture is separated into layers by adding thereto water and ethyl acetate. The organic layer is washed with water three times and concentrated under reduced pressure. The residue is subjected to silica gel column chromatography and eluted with a mixed solvent of chloroform/methanol [4:1 (v/v)] to give the desired product (1.39 g) as oil.

NMR (CDCl$_3$) δ ppm: 7.95 (d, 2H, J=9.0 Hz), 6.86 (d, 2H, J=9.0 Hz), 6.67 (d, 1H, J=8.4 Hz), 6.50 (d, 1H, J=2.4 Hz), 6.38–6.26 (m, 1H), 5.90 (s, 2H), 4.09–3.88 (m, 7H), 3.06–1.39 (m, 11H).

(4) 4-[1-[2-(3,4-Methylenedioxyphenoxy)ethyl]-piperidin-4-yl]methoxybenzoic acid Using methyl 4-[1-[2-(3,4-methylenedioxyphenoxy)ethyl]piperidin-4-yl]methoxybenzoate (1.38 g) as a starting material, the desired product (1.14 g) is obtained in the same manner as in Example 1-(5), m.p. 133°–136° C.

Using the suitable starting materials, the compounds of the following Examples 46–51 are obtained in the same manner as in Example 45.

EXAMPLE 46

(1) Ethyl 1-(piperonyloyl)piperidine-4-carboxylate
NMR (CDCl$_3$) δ ppm: 6.96–6.74 (m, 3H), 5.99 (s, 2H), 4.28–3.90 (m, 4H), 3.20–2.89 (m, 2H), 2.75–2.42 (m, 1H), 2.04–1.60 (m, 4H), 1.26 (t, 3H, J=7.1 Hz).

(2) 1-Piperonyl-4-hydroxymethylpiperidine
NMR (CDCl$_3$) δ ppm: 6.84 (s, 1H), 6.73 (bs, 2H), 5.92 (s, 2H), 3.48 (d, 2H, J=5.1 Hz), 3.40 (s, 2H), 2.95–2.83 (m, 2H), 2.08–1.09 (m, 8H).

(3) Methyl 4-(1-piperonylpiperidin-4-yl)methoxybenzoate
NMR (CDCl$_3$) δ ppm: 7.95 (d, 2H, J=9.0 Hz), 6.92–6.73 (m, 5H), 5.92 (s, 2H), 4.06–3.87 (m, 5H), 3.51 (s, 2H), 2.99–1.25 (m, 9H).

(4) 4-(1-Piperonylpiperidin-4-yl)methoxybenzoic acid, m.p. 164°–168° C. (decomposed)

EXAMPLE 47

(1) Ethyl 1-(piperonyloyl)piperidine-3-carboxylate
NMR (CDCl$_3$) δ ppm: 6.97–6.75 (m, 3H), 5.99 (s, 2H), 4.36–3.91 (m, 4H), 3.33–2.90 (m, 2H), 2.67–2.37 (m, 1H), 2.24–1.53 (m, 4H), 1.24 (t, 3H, J=7.0 Hz).

(2) 3-Hydroxymethyl-1-piperonylpiperidine
NMR (CDCl$_3$) δ ppm: 6.82 (s, 1H), 6.73 (bs, 2H), 5.92 (s, 2H), 3.62–3.54 (m, 2H), 3.38 (s, 2H), 2.80–2.45 (m, 2H), 2.20–1.47 (m, 8H).

(3) Methyl 4-(1-piperonylpiperidin-3-yl)methoxybenzoate
NMR (CDCl$_3$) δ ppm: 7.95 (d, 2H, J=9.0 Hz), 6.92–6.71 (m, 5H), 5.92 (s, 2H), 3.91–3.84 (m, 5H), 3.41 (s, 2H), 2.99–2.61 (m, 2H), 2.28–0.88 (m, 7H).

(4) 4-(1-Piperonylpiperidin-3-yl)methoxybenzoic acid, m.p. 213°–216° C. (decomposed)

EXAMPLE 48

(1) Ethyl 1-(3,4-methylenedioxyphenylacetyl)-piperidine-3-carboxylate
NMR (CDCl$_3$) δ ppm: 6.80–6.61 (m, 3H), 5.93 (s, 2H), 4.68–2.76 (m, 8H), 2.57–1.17 (m, 8H)

(2) 1-[2-(3,4-Methylenedioxyphenyl)ethyl]-3-hydroxymethylpiperidine
NMR (CDCl$_3$) δ ppm: 6.81–6.61 (m, 3H), 5.90 (s, 2H), 3.64–3.54 (m, 2H), 2.96–1.51 (m, 14H).

(3) Methyl 4-[1-[2-(3,4-methylenedioxyphenyl)-ethyl]piperidin-3-yl]methoxybenzoate
NMR (CDCl$_3$) δ ppm: 7.97 (d, 2H, J=9.0 Hz), 6.94–6.56 (m, 5H), 5.90 (s, 2H), 3.88 (bs, 5H), 3.12–2.44 (m, 6H), 2.24–1.54 (m, 6H), 1.34–0.91 (b, 1H).

(4) 4-[1-[2-(3,4-Methylenedioxyphenyl)ethyl]-piperidin-3-yl]methoxybenzoic acid, m.p. 92°–95° C.

EXAMPLE 49

(1) Ethyl 1-(3,4-methylenedioxyphenylacetyl)-piperidine-4-carboxylate
NMR (CDCl$_3$) δ ppm: 6.81–6.60 (m, 3H), 5.93 (s, 2H), 4.47–3.37 (m, 6H), 3.24–2.33 (m, 3H), 2.07–1.00 (m, 7H).

(2) 1-[2-(3,4-Methylenedioxyphenyl)ethyl]-4-hydroxymethylpiperidine
NMR (CDCl$_3$) δ ppm: 6.77–6.56 (m, 3H), 5.91 (s, 2H), 3.50 (d, 2H, J=5.3 Hz), 3.07–2.41 (m, 6H), 2.14–1.15 (m, 8H).

(3) Methyl 4-[1-[2-(3,4-methylenedioxyphenyl)-ethyl]piperidin-4-yl]methoxybenzoate
NMR (CDCl$_3$) δ ppm: 7.96 (d, 2H, J=9.0 Hz), 6.93–6.57 (m, 5H), 5.90 (s, 2H), 4.09–3.88 (m, 5H), 3.00–1.78 (m, 12H), 1.62–1.22 (b, 1H).

(4) 4-[1-[2-(3,4-Methylenedioxyphenyl)ethyl]-piperidin-4-yl]methoxybenzoic acid, m.p. 113°–116° C.

EXAMPLE 50

(1) Ethyl 1-(4-tert-butylbenzoyl)piperidine-3-carboxylate
NMR (CDCl$_3$) δ ppm: 7.48–7.25 (m, 4H), 4.39–3.83 (m, 4H), 3.31–2.87 (m, 2H), 2.66–2.37 (b, 1H), 1.92–1.48 (m, 4H), 1.32–1.15 (m, 12H).

(2) 1-(4-tert-Butylbenzyl)-3-hydroxymethylpiperidine
NMR (CDCl$_3$) δ ppm: 7.38–7.18 (m, 4H), 3.63–3.55 (m, 2H), 3.44 (s, 2H), 2.83–2.44 (m, 2H), 2.32–1.47 (m, 8H), 1.31 (s, 9H).

(3) Methyl 4-[1-(4-tert-butylbenzyl)piperidin-3-yl]methoxybenzoate
NMR (CDCl$_3$) δ ppm: 7.96 (d, 2H, J=9.0 Hz), 7.38–7.16 (m, 4H), 6.87 (d, 2H, J=9.0 Hz), 3.92–3.88 (m, 5H), 3.49 (bs, 2H), 2.99–2.61 (m, 2H), 2.27–1.49 (m, 6H), 1.39–0.89 (b, 10H).

(4) 4-[1-(4-tert-Butylbenzyl)piperidin-3-yl]-methoxybenzoic acid, m.p. 241°–244° C. (decomposed)

EXAMPLE 51

(1) Ethyl 1-(4-chlorobenzoyl)piperidine-3-carboxylate
NMR (CDCl$_3$) δ ppm: 7.36 (bs, 4H), 4.67–3.50 (m, 4H), 3.35–2.93 (m, 2H), 2.70–2.33 (m, 1H), 2.27–1.16 (m, 7H).

(2) 1-(4-Chlorobenzyl)-3-hydroxymethylpiperidine
NMR (CDCl$_3$) δ ppm: 7.36–7.15 (m, 4H), 3.76–3.43 (m, 4H), 2.81–2.47 (m, 2H), 2.27–1.46 (m, 8H).

(3) Methyl 4-[1-(4-chlorobenzyl)piperidin-3-yl]methoxybenzoate
NMR (CDCl$_3$) δ ppm: 7.96 (d, 2H, J=9.0 Hz), 7.24 (bs, 4H), 6.86 (d, 2H, J=9.0 Hz), 3.91–3.85 (m, 5H), 3.46 (bs, 2H), 2.98–2.53 (m, 2H), 2.25–1.48 (m, 6H), 1.36–0.80 (m, 1H).

(4) 4-[1-(4-Chlorobenzyl)piperidin-3-yl]methoxybenzoic acid, m.p. 149°–151° C. (decomposed)

EXAMPLE 52

(1) 1-(4-Chlorophenyl)-3-hydroxymethylpyrrolidine
Lithium aluminum hydride (2.93 g) is suspended in THF (90 ml) under ice-cooling and thereto is added 1-(4-chlorophenyl)-5-oxo-3-pyrrolidinecarboxylic acid (4.63 g) in portions. The mixture is stirred under refluxing for 20 hours. Ethyl acetate and a small amount of 1N aqueous sodium hydroxide solution are added to the reaction mixture to decompose the excess reducing agent. The mixture is filtered and the filtrate is concentrated under reduced pressure. The residue is subjected to silica gel column chromatography and eluted with a mixed solvent of chloroform/methanol [40:1 (v/v)]to give the desired product (4.00 g).

NMR (CDCl₃) δ ppm: 7.14 (d, 2H, J=8.9 Hz), 6.45 (d, 2H, J=8.9 Hz), 3.66 (d, 2H, J=6.4 Hz), 3.49–2.99 (m, 4H), 2.71–1.63 (m, 4H).

(2) Methyl 4-[1-(4-chlorophenyl)pyrrolidin-3-yl]methoxybenzoate

Using 1-(4-chlorophenyl)-3-hydroxymethylpyrrolidine (3.99 g) as a starting material, the desired product (3.78 g) is obtained in the same manner as in Example 1–(4).

NMR (CDCl₃) δ ppm: 7.99 (d, 2H, J=9.0 Hz), 7.16 (d, 2H, J=9.0 Hz), 6.91 (d, 2H, J=9.0 Hz), 6.48 (d, 2H. J=9.0 Hz), 4.03 (d, 2H, J=6.6 Hz), 3.88 (s, 3H), 3.61–2.70 (m, 5H), 2.43–1.82 (m, 2H).

(3) 4-[1-(4-Chlorophenyl)pyrrolidin-3-yl]methoxybenzoic acid

Using methyl 4-[1-(4-chlorophenyl)pyrrolidin-3-yl]methoxybenzoate (3.77 g) as a starting material, the desired product (3.20 g) is obtained in the same manner as in Example 1–(5), m.p. 200°–203° C. (decomposed)

EXAMPLES 53–56

Using the suitable starting materials, the compounds of the following Examples 53–56 are obtained in the same manner as in Example 52.

EXAMPLE 53

(1) 1-(4-tert-Butylphenyl)-3-hydroxymethylpyrrolidine

NMR (CDCl₃) δ ppm: 7.26 (d, 2H, J=8.9 Hz), 6.54 (d, 2H, J=8.9 Hz), 3.65 (d, 2H, J=6.4 Hz), 3.51–3.03 (m, 4H), 2.69–1.60 (m, 4H), 1.29 (s, 9H)

(2) Methyl 4-[1-(4-tert-butylphenyl)pyrrolidin-3-yl]methoxybenzoate, m.p. 103°–105° C.

(3) 4-[1-(4-tert-Butylphenyl)pyrrolidin-3-yl]methoxybenzoic acid, m.p. 214°–217° C. (decomposed)

EXAMPLE 54

(1) 1-[4-(4-tert-Butylphenoxy)phenyl]-5-oxo-3-pyrrolidinecarboxylic acid, m.p. 191°–193° C.

(2) 1-[4-(4-tert-Butylphenoxy)phenyl]-3-hydroxymethylpyrrolidine

NMR (CDCl₃) δ ppm: 7.28 (d, 2H, J=8.9 Hz), 7.01–6.79 (m, 4H), 6.54 (d, 2H, J=8.9 Hz), 3.69 (d, 2H, J=6.6 Hz), 3.52–3.03 (m, 4H), 2.72–1.62 (m, 4H), 1.30 (s, 9H).

(3) Methyl 4-[1-[4-(4-tert-butylphenoxy)phenyl]-pyrrolidin-3-yl]methoxybenzoate

NMR (CDCl₃) δ ppm: 7.99 (d, 2H, J=9.0 Hz), 7.27 (d, 2H, J=8.8 Hz), 7.02–6.79 (m, 6H), 6.55 (d, 2H, J=9.0 Hz), 4.03 (d, 2H, J=6.8 Hz), 3.88 (s, 3H), 3.61–2.70 (m, 5H), 2.43–1.73 (m, 2H), 1.29 (s, 9H).

(4) 4-[1-[4-(4-tert-Butylphenoxy)phenyl]pyrrolidin-3-yl]methoxybenzoic acid, m.p. 172°–175° C.

EXAMPLE 55

(1) 1-[4-(4-Chlorophenoxy)phenyl]-3-hydroxymethylpyrrolidine

NMR (CDCl₃) δ ppm: 7.20 (d, 2H, J=9.1 Hz), 6.98–6.78 (m, 4H), 6.54 (d, 2H, J=9.1 Hz), 3.69 (d, 2H, J=6.4 Hz), 3.52–3.03 (m, 4H), 2.73–1.60 (m, 4H).

(2) Methyl 4-[1-[4-(4-chlorophenoxy)phenyl]-pyrrolidin-3-yl]methoxybenzoate, m.p. 99°–103° C.

(3) 4-[1-[4-(4-Chlorophenoxy)phenyl]pyrrolidin-3-yl]methoxybenzoic acid hydrochloride The same procedure as in Example 1–(5) is repeated to give 4-[1-[4-(4-chlorophenoxy)phenyl]pyrrolidin-3-yl]methoxybenzoic acid, then followed by converting it to the hydrochloride thereof by a conventional method to give the desired product, m.p. 199°–202° C. (decomposed).

EXAMPLE 56

(1) 1-(4-Chlorophenyl)-3-hydroxymethylpiperidine

NMR (CDCl₃) δ ppm: 7.17 (d, 2H, J=9.1 Hz), 6.87 (d, 2H, J=9.1 Hz), 3.73–3.37 (m, 4H), 2.87–2.43 (m, 2H), 1.98–1.51 (m, 6H).

(2) Methyl 4-[1-(4-chlorophenyl)piperidin-3-yl]methoxybenzoate hydrochloride

The same procedure as in Example 1–(4) is repeated to give methyl 4-[1-(4-chlorophenyl)piperidin-3-yl]methoxybenzoate, followed by converting it to the hydrochloride thereof by a conventional method to give the desired product.

NMR (CDCl₃) δ ppm: 8.03–7.86 (m, 4H), 7.49 (d, 2H, J=9.0 Hz), 6.87 (d, 2H, J=9.0 Hz), 4.05–3.54 (m, 7H), 3.43–2.54 (m, 4H), 2.21–1.11 (m, 4H).

(3) 4-[1-(4-Chlorophenyl)piperidin-3-yl]methoxybenzoic acid, m.p. 214°–217° C. (decomposed)

EXAMPLE 57

(1) Methyl 4-[1-(4-methanesulfonyloxyphenyl)-2-pyrrolidon-4-yl]methoxybenzoate

Methyl 4-[1-(4-hydroxyphenyl)-2-pyrrolidon-4-yl]methoxybenzoate (1.50 g) is suspended in methylene chloride (15 ml) and thereto are added dropwise methanesulfonyl chloride (0.68 ml) and triethylamine (1.82 ml) with stirring under ice-cooling. Further, the mixture is stirred at room temperature for 19 hours. The reaction mixture is concentrated under reduced pressure and ethyl acetate (80 ml) is added to the residue. The mixture is washed with water three times, dried over anhydrous magnesium sulfate and concentrated under reduced pressure to give the desired product 79 g) as crystal, m.p. 111°–113° C.

(2) 4-[1-(4-Methanesulfonyloxyphenyl)-2-pyrrolidon-4-yl]methoxybenzoic acid

Methyl 4-[1-(4-methanesulfonyloxyphenyl)-2-pyrrolidon-4-yl]methoxybenzoate (1.78 g) is dissolved in dioxane (20 ml) and thereto is added a solution of sodium hydroxide (0.34 g) in water (5 ml). The mixture is stirred at room temperature for 16 hours. After adding conc. hydrochloric acid (about 0.7 ml), the reaction mixture is concentrated under reduced pressure. Water is added to the resulting residue and the precipitate is collected by filtration, washed with water and recrystallized from about 15% aqueous methanol to give the desired product (1.43 g), m.p. 199°–201° C.

EXAMPLES 58–62

Using the suitable starting materials, the compounds of the following Examples 58–62 are obtained in the same manner as in Example 57.

EXAMPLE 58

(1) Methyl 4-[1-(4-ethanesulfonyloxyphenyl)-2-pyrrolidon-4-yl]methoxybenzoate, m.p. 100°–101.5° C.

(2) 4-[1-(4-Ethanesulfonyloxyphenyl)-2-pyrrolidon-4-yl]methoxybenzoic acid, m.p. 210°–211° C.

EXAMPLE 59

(1) Methyl 4-[1-(4-n-propanesulfonyloxyphenyl)-2-pyrrolidon-4-yl]methoxybenzoate, m.p. 107°–109° C.

(2) 4-[1-(4-n-Propanesulfonyloxyphenyl)-2-pyrrolidon-4-yl]methoxybenzoic acid, m.p. 197°–199° C.

EXAMPLE 60

(1) Methyl 4-[1-(4-n-butanesulfonyloxyphenyl)-2-pyrrolidon-4-yl]methoxybenzoate

NMR (CDCl$_3$) δ ppm: 7.99 (d, 2H, J=9.0 Hz), 7.67 (d, 2H, J=9.2 Hz), 7.28 (d, 2H, J=9.2 Hz), 6.91 (d, 2H, J=9.1 Hz), 4.30–3.74 (m, 7H), 3.31–2.49 (m, 5H), 2.12–1.79 (m, 2H), 1.71–1.31 (m, 2H}, 0.97 (t, 3H, J=7.0 Hz).

(2) 4-[1-(4-n-Butanesulfonyloxyphenyl)-2-pyrrolidon-4-yl]methoxybenzoic acid, m.p. 185°–187° C.

EXAMPLE 61

(1) Methyl 4-[1-(4-benzenesulfonyloxyphenyl)-2-pyrrolidon-4-yl]methoxybenzoate

NMR (CDCl$_3$) δ ppm: 8.04–7.43 (m, 9H), 7.02–6.85 (m, 4H), 4.16–3.69 (m, 7H), 3.15–2.35 (m, 3H).

(2) 4-[1-(4-Benzenesulfonyloxyphenyl)-2-pyrrolidon-4-yl]methoxybenzoic acid, m.p. 196°–198° C.

EXAMPLE 62

(1) Methyl 4-[1-[4-(4-chlorobenzenesulfonyl)oxyphenyl]-2-pyrrolidon-4-yl]methoxybenzoate NMR (CDCl$_3$) δ ppm: 8.04–7.94 (d, 2H, J=9.0 Hz), 7.80–7.43 (m, 6H), 7.03–6.85 (m, 4H), 4.16–3.71 (m, 7H), 3.15–2.36 (m, 3H).

(2) 4-[1-[4-(4-Chlorobenzenesulfonyl)oxyphenyl]-2-pyrrolidon-4-yl]methoxybenzoic acid, m.p. 197°–199° C.

EXAMPLES 63–69

Using the suitable starting materials, the compounds of the following Examples 63–69 are obtained in the same manner as in Example 1.

EXAMPLE 63

(1) 1-(4-Isobutyrylaminophenyl)-5-oxo-3-pyrrolidinecarboxylic acid, m.p. 203°–206° C.

(2) Methyl 1-(4-isobutyrylaminophenyl)-5-oxo-3-pyrrolidinecarboxylate, m.p. 143°–145° C.

(3) 1-(4-Isobutyrylaminophenyl)-4-hydroxymethyl-2-pyrrolidone, m.p. 157°–159° C.

(4) Methyl 4-[1-(4-isobutyrylaminophenyl)-2-pyrrolidon-4-yl]methoxybenzoate, m.p. 175°–177° C.

(5) 4-[1-(4-Isobutyrylaminophenyl)-2-pyrrolidon-4-yl]methoxybenzoic acid, m.p. 245°–246° C.

EXAMPLE 64

(1) 1-(4-Pivaloylaminophenyl)-5-oxo-3-pyrrolidinecarboxylic acid

NMR (DMSO-d6) δ ppm: 9.17 (bs, 1H), 7.70–7.47 (m, 4H), 4.04–3.95 (m, 2H), 3.52–3.18 (m, 1H), 2.72 (d, 2H, J=8.1 Hz), 1.22 (s, 9H).

(2) Methyl 1-(4-pivaloylaminophenyl)-5-oxo-3-pyrrolidinecarboxylate, m.p. 154.4°–157° C.

(3) 1-(4-Pivaloylaminophenyl)-4-hydroxymethyl-2-pyrrolidone, m.p. 198°–201° C.

(4) Methyl 4-[1-(4-pivaloylaminophenyl)-2-pyrrolidon-4-yl]methoxybenzoate

NMR (CDCl$_3$) δ ppm: 9.08 (bs, 1H), 7.92 (d, 2H, J=9.0 Hz), 7.72–7.48 (m, 4H), 7.02 (d, 2H, J=9.0 Hz), 4.18–3.65 (m, 7H), 3.06–2.32 (m, 3H), 1.24 (s, 9H).

(5) 4-[1-(4-Pivaloylaminophenyl)-2-pyrrolidon-4-yl]methoxybenzoic acid, m.p. 264°–266° C.

EXAMPLE 65

(1) 1-(4-Acetylaminophenyl)-5-oxo-3-pyrrolidinecarboxylic acid

NMR (DMSO-d6) δ ppm: 9.89 (bs, 1H), 7.56 (s, 4H), 4.03–3.93 (m, 2H), 3.51–3.18 (m, 1H), 2.77–2.67 (m, 2H), 2.03 (s, 3H).

(2) Methyl 1-(4-acetylaminophenyl)-5-oxo-3-pyrrolidinecarboxylate

NMR (DMSO-d$_6$) δ ppm: 9.82 (bs, 1H), 7.67–7.45 (m, 4H), 4.07–3.97 (m, 2H), 3.70–3.21 (m, 4H), 2.76 (d, 2H, J=7.7 Hz), 2.04 (s, 3H).

(3) 1-(4-Acetylaminophenyl)-4-hydroxymethyl-2-pyrrolidone, m.p. 159°–162° C.

(4) Methyl 4-[1-(4-acetylaminophenyl)-2-pyrrolidon-4-yl]methoxybenzoate, m.p. 177°–180° C.

(5) 4-[1-(4-Acetylaminophenyl)-2-pyrrolidon-4-yl]methoxybenzoic acid, m.p. 240.5°–242.5° C.

EXAMPLE 66

(1) 1-(4-Benzoylaminophenyl)-5-oxo-3-pyrrolidinecarboxylic acid

NMR (DMSO-d6) δ ppm: 8.02–7.46 (m, 10H), 4.07–3.98 (m, 2H), 3.54–3.20 (m, 1H), 2.79–2.69 (m, 2H).

(2) Methyl 1-(4-benzoylaminophenyl)-5-oxo-3-pyrrolidinecarboxylate, m.p. 191°–194° C.

(3) 1-(4-Benzoylaminophenyl)-4-hydroxymethyl-2-pyrrolidone

NMR (DMSO-d6) δ ppm: 8.02–7.43 (m, 10H), 5.25–4.29 (b, 1H), 4.14–3.00 (m, 4H), 2.87–2.12 (m, 3H).

(4) Methyl 4-[1-(4-benzoylaminophenyl)-2-pyrrolidon-4-yl]methoxybenzoate, m.p. 236°–238° C.

(5) 4-[1-(4-Benzoylaminophenyl)-2-pyrrolidon-4-yl]methoxybenzoic acid, m.p. 271°–274° C.

EXAMPLE 67

(1) 1-(2,4-Dimethoxyphenyl)-5-oxo-3-pyrrolidinecarboxylic acid, m.p. 183.5°–185° C.

(2) Methyl 1-(2,4-dimethoxyphenyl)-5-oxo-3-pyrrolidinecarboxylate

NMR (CDCl$_3$) δ ppm: 7.14 (d, 1H, J=9.2 Hz), 6.57–6.44 (m, 2H), 3.94–3.77 (m, 11H), 3.57–3.21 (m, 1H), 2.87–2.76 (m, 2H).

(3) 1-(2,4-Dimethoxyphenyl)-4-hydroxymethyl-2-pyrrolidone

NMR (CDCl$_3$) δ ppm: 7.10 (d, 1H, J=9.2 Hz), 6.54–6.41 (m, 2H), 3.88–3.41 (m, 10H), 2.99–2.16 (m, 4H).

(4) Methyl 4-[1-(2,4-dimethoxyphenyl)-2-pyrrolidon-4-yl]methoxybenzoate

NMR (CDCl$_3$) δ ppm: 8.00 (d, 2H, J=9.0 Hz), 7.13 (d, 1H, J=9.2 Hz), 6.93 (d, 2H, J=9.0 Hz), 6.55–6.42 (m, 2H), 4.10 (d, 2H, J=6.6 Hz), 3.89–3.57 (m, 11H), 3.12–2.26 (m, 3H).

(5) 4-[1-(2,4-Dimethoxyphenyl)-2-pyrrolidon-4-yl]methoxybenzoic acid, m.p. 198°–200° C.

EXAMPLE 68

(1) 1-(3,4-Dimethoxyphenyl)-5-oxo-3-pyrrolidinecarboxylic acid, m.p. 194°–195.5° C.

(2) Methyl 1-(3,4-dimethoxyphenyl)-5-oxo-3-pyrrolidinecarboxylate

NMR (CDCl$_3$) δ ppm: 7.44 (bs, 1H), 6.84 (d, 2H, J=1.3 Hz), 4.09–3.78 (m, 11H), 3.55–3.19 (m, 1H), 2.93–2.82 (m, 2H).

(3) 1-(3,4-Dimethoxyphenyl)-4-hydroxymethyl-2-pyrrolidone

NMR (CDCl$_3$) δ ppm: 7.46 (s, 1H), 6.97–6.77 (m, 2H), 4.03–3.50 (m, 10H), 2.87–1.93 (m, 4H)

(4) Methyl 4-[1-(3,4-dimethoxyphenyl)-2-pyrrolidon-4-yl]methoxybenzoate, m.p. 145.5°–147.5° C.

(5) 4-[1-(3,4-Dimethoxyphenyl)-2-pyrrolidon-4-yl]methoxybenzoic acid, m.p. 181°–182° C.

EXAMPLE 69

(1) 1-(2,5-Dimethoxyphenyl)-5-oxo-3-pyrrolidinecarboxylic acid

NMR (CDCl$_3$) δ ppm: 6.84 (s, 3H), 3.97 (d, 2H, J=7.3 Hz), 3.78 (s, 3H), 3.75 (s, 3H), 3.60–3.25 (m, 1H), 2.93–2.82 (m, 2H).

(2) Methyl 1-(2,5-dimethoxyphenyl)-5-oxo-3-pyrrolidinecarboxylate

NMR (CDCl$_3$) δ ppm: 6.85 (s, 3H), 3.95 (d, 2H, J=7.0 Hz), 3.77 (bs, 9H), 3.60–3.24 (m, 1H), 2.89–2.77 (m, 2H).

(3) 1-(2,5-Dimethoxyphenyl)-4-hydroxymethyl-2-pyrrolidone

NMR (CDCl$_3$) δ ppm: 6.97–6.72 (m, 3H), 3.98–3.51 (m, 10H), 2.85–1.78 (m, 4H).

(4) Methyl 4-[1-(2,5-dimethoxyphenyl)-2-pyrrolidon-yl]methoxybenzoate

NMR (CDCl$_3$) δ ppm: 8.00 (d, 2H, J=8.8 Hz), 6.98–6.84 (m, 5H), 4.10 (d, 2H, J=6.4 Hz), 4.00–3.63 (m, 11H), 3.15–2.29 (m, 3H).

(5) 4-[1-(2,5-Dimethoxyphenyl)-2-pyrrolidon-4-yl]methoxybenzoic acid, m.p. 168°–169.5° C.

EXAMPLE 70

(1) Methyl 4-[1-(4-aminophenyl)-2-pyrrolidon-4-yl]methoxybenzoate

Methyl 4-[1-(4-acetylaminophenyl)-2-pyrrolidon-4-yl]methoxybenzoate (1.70 g) is dissolved in methanol (30 ml) and thereto is added conc. sulfuric acid (0.24 ml). The mixture is stirred under refluxing for 23 hours. Subsequently, the reaction solution is concentrated under reduced pressure, and water and the neutralization amount of sodium hydrogen carbonate are added to the resulting residue. The precipitated crystal is collected by filtration and washed with water to give the desired product (1.47 g), m.p. 136°–138° C.

(2) 4-[1-(4-Aminophenyl)-2-pyrrolidon-4-yl]methoxybenzoic acid is obtained in the same manner as in Example 1-(5), m.p. 204°–207° C.

EXAMPLES 71–73

Using the suitable starting materials, the compounds of the following Examples 71–73 are obtained in the same manner as in Example 27–(3)–(6).

EXAMPLE 71

(1) Methyl 1-(4-allyloxyphenyl)-5-oxo-3-pyrrolidinecarboxylate, m.p. 62.5°–64.5° C.

(2) 1-(4-Allyloxyphenyl)-4-hydroxymethyl-2-pyrrolidone, m.p. 79°–81° C.

(3) Methyl 4-[1-(4-allyloxyphenyl)-2-pyrrolidon-4-yl]methoxybenzoate, m.p. 83°–84° C.

(4) 4-[1-(4-allyloxyphenyl)-2-pyrrolidon-4-yl]methoxybenzoic acid, m.p. 180°–181.5° C.

EXAMPLE 72

(1) Methyl 1-(4-methallyloxyphenyl)-5-oxo-3-pyrrolidinecarboxylate, m.p. 58°–61° C.

(2) 1-(4-Methallyloxyphenyl)-4-hydroxymethyl-2-pyrrolidone

NMR (CDCl$_3$) δ ppm: 7.47 (d, 2H, J=9.0 Hz), 6.90 (d, 2H, J=9.0 Hz), 5.02 (d, 2H, J=8.8 Hz), 4.41 (s, 2H), 4.01–3.53 (m, 4H), 2.88–2.21 (m, 3H), 2.13–1.91 (b, 1H), 1.81 (s, 3H).

(3) Methyl 4-[1-(4-methallyloxyphenyl)-2-pyrrolidon-yl]methoxybenzoate, m.p. 99°–100° C.

(4) 4-[1-(4-Methallyloxyphenyl)-2-pyrrolidon-4-yl]methoxybenzoic acid, m.p. 192°–194° C.

EXAMPLE 73

(1) Methyl 1-[4-(2-benzyloxyethoxy)phenyl]-5-oxo-3-pyrrolidinecarboxylate

NMR (CDCl$_3$) δ ppm: 7.51–7.28 (m, 7H), 6.91 (d, 2H, J=9.2 Hz), 4.62 (s, 2H), 4.19–3.63 (m, 9H), 3.54–3.18 (m, 1H), 2.92–2.81 (m, 2H).

(2) 1-[4-(2-Benzyloxyethoxy)phenyl]-4-hydroxymethyl-2-pyrrolidone

NMR (CDCl$_3$) δ ppm: 7.47 (d, 2H, J=9.0 Hz), 7.33 (bs, 5H), 6.90 (d, 2H, J=9.0 Hz), 4.62 (s, 2H), 4.18–3.50 (m, 8H), 2.89–1.98 (m, 4H).

(3) Methyl 4-[1-[4-(2-benzyloxyethoxy)phenyl]-2-pyrrolidon-4-yl]methoxybenzoate, m.p. 86°–89° C.

(4) 4-[1-[4-(2-Benzyloxyethoxy)phenyl]-2-pyrrolidon-4-yl]methoxybenzoic acid, m.p. 143°–144° C.

EXAMPLE 74

(1) Methyl 4-[1-[4-(2-hydroxyethoxy)phenyl]-2-pyrrolidon-4-yl]methoxybenzoate

Using methyl 4-[1-[4-(2-benzyloxyethoxy)phenyl]-2-pyrrolidon-4-yl]methoxybenzoate (13.0 g) as a starting material, the desired product (9.38 g) is obtained in the same manner as in Example 34–(1), m.p. 129°–131° C.

(2) 4-[1-[4-(2-Hydroxyethoxy)phenyl]-2-pyrrolidon-4-yl]methoxybenzoic acid is obtained in the same manner as in Example 1-(5), m.p. 207°–209° C.

EXAMPLE 75

(1) Methyl 4-[1-(4-isobutoxyphenyl)-2-pyrrolidon-4-yl]methoxybenzoate

Methyl 4-[1-(4-hydroxyphenyl)-2-pyrrolidon-4-yl]methoxybenzoate (2.00 g), isobutyl bromide (2.58 ml) and potassium carbonate (3.24 g) are dissolved and suspended in dimethylformamide (20 ml) and the mixture is heated with stirring at 80° C. for 24 hours. The solvent is distilled off under reduced pressure and water is added to the resulting residue. The resulting precipitate is collected by filtration and recrystallized from about 20% aqueous methanol to give the desired product (2.11 g}, m.p. 117.5°–118.5° C.

(2) 4-[1-(4-Isobutoxyphenyl)-2-pyrrolidon-4-yl]methoxybenzoic acid is obtained in the same manner as in Example 1-(5), m.p. 203°–204.5° C.

EXAMPLES 76–81

Using the suitable starting materials, the compounds of the following Examples 76–81 are obtained in the same manner as in Example 75.

EXAMPLE 76

(1) Methyl 4-[1-(4-isopentyloxyphenyl)-2-pyrrolidon-4-yl]methoxybenzoate, m.p. 114°–115° C.

(2) 4-[1-(4-Isopentyloxyphenyl)-2-pyrrolidon-4-yl]methoxybenzoic acid, m.p. 197.5°–198.5° C.

EXAMPLE 77

(1) Methyl 4-[1-(4-n-pentyloxyphenyl)-2-pyrrolidon-4-yl]methoxybenzoate, m.p. 112.5°–114° C.

(2) 4-[1-(4-n-Pentyloxyphenyl)-2-pyrrolidon-4-yl]methoxybenzoic acid, m.p. 190°–191° C.

EXAMPLE 78

(1) Methyl 4-[1-(4-n-hexyloxyphenyl)-2-pyrrolidon-4-yl]methoxybenzoate, m.p. 108.5°–109.5° C.

(2) 4-[1-(4-n-Hexyloxyphenyl)-2-pyrrolidon-4-yl]methoxybenzoic acid, m.p. 193°–194° C.

EXAMPLE 79

(1) Methyl 4-[1-[4-(4-methoxybenzyloxy)phenyl]-2-pyrrolidon-4-yl]methoxybenzoate, m.p. 114°–115.5° C.

(2) 4-[1-[4-(4-Methoxybenzyloxy)phenyl]-2-pyrrolidon-4-yl]methoxybenzoic acid, m.p. 207.5°–208.5° C.

EXAMPLE 80

(1) Methyl 4-[1-(4-cyclopentyloxyphenyl)-2-pyrrolidon- 4-yl]methoxybenzoate, m.p. 110°–111° C.

(2) 4-[1-(4-Cyclopentyloxyphenyl)-2-pyrrolidon-4-yl]methoxybenzoic acid, m.p. 194.5°–196° C.

EXAMPLE 81

(1) Methyl 4-[1-(4-cyclohexylmethoxyphenyl)-2-pyrrolidon-4-yl]methoxybenzoate, m.p. 155°–156.5° C.

(2) 4-[1-(4-Cyclohexylmethoxyphenyl)-2-pyrrolidon-4-yl]methoxybenzoic acid, m.p. 220°–222° C.

EXAMPLE 82

(1) Methyl 4-[1-[4-(2-methanesulfonyloxyethoxy)phenyl]-2-pyrrolidon-4-yl]methoxybenzoate Methyl 4-[1-[4-(2-hydroxyethoxy)phenyl]-2-pyrrolidon-4-yl]methoxybenzoate (3.00 g) is dissolved in methylene chloride (30 ml) and the mixture is cooled with ice. Thereto are added methanesulfonyl chloride (0.90 ml) and triethylamine (2.16 ml) severally and the mixture is stirred at room temperature for 16 hours. The reaction mixture is concentrated under reduced pressure and ethyl acetate (60 ml) is added to the residue. The mixture is washed with water three times, dried over anhydrous magnesium sulfate and concentrated under reduced pressure. The residue is subjected to silica gel column chromatography and eluted with chloroform to give the desired product (3.39 g) as powder.

Analysis Calc'd for $C_{22}H_{25}NO_8S$ (M.W.: 463.509): C: 57.01%, H: 5.44%, N: 3.02%. Found: C: 56.86%, H: 5.48%, N: 2.78%.

(2) Methyl 4-[1-[4-[2-(1-imidazolyl)ethoxy]phenyl]-2-pyrrolidon-4-yl]methoxybenzoate Imidazole (0.53 g) is dissolved in dimethylformamide (2.5 ml) and purged with nitrogen gas. Thereto is added 60% sodium hydride (0.31 g) and the mixture is heated with stirring at 80° C. for 20 minutes. The reaction mixture is cooled to room temperature and thereto is added a solution of methyl 4-[1-[4-(2-methanesulfonyloxyethoxy)phenyl]-2-pyrrolidon-4-yl]methoxybenzoate (3.35 g) in dimethylformamide (5.0 ml). The mixture is heated again with stirring at 80° C. for 4 hours and concentrated under reduced pressure. The resulting residue is washed with n-hexane three times, and dissolved in ethyl acetate (80 ml). The mixture is washed with water three times, dried over anhydrous magnesium sulfate and concentrated under reduced pressure. The residue is subjected to silica gel column chromatography and washed with chloroform, and then eluted with a mixed solvent of chloroform/methanol [20:1 (v/v)]. The eluate is concentrated under reduced pressure and crystallized from about 30% aqueous methanol to give the desired product (2.53 g), m.p. 135°–138° C.

(3) 4-[1-[4-[2-(1-Imidazolyl)ethoxy]phenyl]-2-pyrrolidon-4-yl]methoxybenzoic acid is obtained in the same manner as in Example 1–(5), m.p. 241°–244° C.

EXAMPLE 83

(1) Methyl 4-[1-(4-bromomethylphenyl)-2-pyrrolidon-4-yl]methoxybenzoate

Methyl 4-[1-(4-tolyl)-2-pyrrolidon-4-yl]methoxybenzoate (3.00 g) and N-bromosuccinimide (1.81 g) are suspended in carbon tetrachloride (50 ml), and thereto is added benzoyl peroxide (0.21 g) and the mixture is stirred under refluxing for 5 hours. The reaction mixture is filtered and the filtrate is concentrated under reduced pressure. The residue is dissolved in ethyl acetate (60 ml), washed successively with aqueous sodium hydrogen carbonate solution and water, dried over anhydrous magnesium sulfate and concentrated under reduced pressure. The resulting oily product is subjected to silica gel column chromatography and eluted with a mixed solvent of chloroform/n-hexane [1:1 (v/v)] to give the desired product (2.10 g).

Analysis Calc'd for $C_{20}H_{20}BrNO_4$ (M.W. 418.291): C: 57.43%, H: 4.82%, N: 3.35%. Found; C: 57.58%, H: 4.85%, N: 3.17%.

(2) Methyl 4-[1-[4-(1-imidazolyl)methylphenyl]-2-pyrrolidon-4-yl]methoxybenzoate Using methyl 4-[1-(4-bromomethylphenyl)-2-pyrrolidon-4-yl]methoxybenzoate (2.06 g) as a starting material, the above desired product (1.50 g) is obtained in the same manner as in Example 82–(2) as amorphous.

NMR (CDCl$_3$) δ ppm: 7.99 (d, 2H, J=8.8 Hz), 7.63 (d, 2H, J=8.8 Hz), 7.52 (s, 1H), 7.16 (d, 2H, J=8.8 Hz), 7.07 (s, 1H), 6.96–6. 86 (m, 3H), 5.08 (s, 2H), 4.16–3.72 (m, 7H), 3.17–2.32 (m, 3H).

(3) 4-[1-[4-(1-Imidazolyl)methylphenyl]-2-pyrrolidon-4-yl]methoxybenzoic acid is obtained in the same manner as in Example 1–(5), m.p. 250°–253° C. (decomposed).

EXAMPLE 84

(1) Methyl 4-[1-(4-tert-butoxyphenyl)-2-pyrrolidon-4-yl]methoxybenzoate tert-Butanol (1.58 g), dicyclohexylcarbodiimide (4.04 g) and cuprous chloride (35 mg) are suspended in methylene chloride (5 ml) and the mixture is stirred at room temperature under shading for 4 days. Thereto is added a suspension of methyl 4-[1-(4-hydroxyphenyl)-2-pyrrolidon-4-yl]methoxybenzoate (1.52 g) in methylene chloride (30 ml) and the mixture is further stirred for 14 hours. The reaction mixture is concentrated under reduced pressure and thereto is added chloroform. The insoluble material is removed by filtration and the filtrate is subjected to silica gel column chromatography and eluted with chloroform to give the desired product (0.93 g), m.p. 126°–127.5° C.

(2) 4-[1-(4-tert-Butoxyphenyl)-2-pyrrolidon-4-yl]methoxybenzoic acid is obtained in the same manner as in Example 1–(5), m.p 203°–205° C.

EXAMPLE 85

(1) Methyl 4-[1-[4-(2-hydroxy-2-methylpropoxy)phenyl] -2-pyrrolidon-4-yl]methoxybenzoate Methyl 4-[1-[4-hydroxyphenyl)-2-pyrrolidon-4-yl]methoxybenzoate (2.00 g) and potassium carbonate (1.62 g) are dissolved and suspended in dimethylformamide (20 ml) and thereto is added isobutylene oxide (1.06 ml). The mixture is stirred at 80° C. for 17 hours and thereto is added isobutylene oxide (1.06 ml), and the mixture is further heated with stirring for 5 hours. The reaction mixture is concentrated under reduced pressure and thereto is added water. The insoluble material is collected by filtration, washed with water and recrystallized from about 30% aqueous methanol to give the desired product (2.15 g), m.p. 89.5°–90.5° C.

(2) 4-[1-[4-(2-Hydroxy-2-methylpropoxy)phenyl]-2-pyrrolidon-4-yl]methoxybenzoic acid is obtained in the same manner as in Example 1–(5), m.p. 175°–176° C.

EXAMPLE 86

4-[1-[4-(2-Hydroxycyclohexyloxy)phenyl]-2-pyrrolidon-4-yl]methoxybenzoic acid

Methyl 4-[1-(4-hydroxyphenyl]-2-pyrrolidon-4-yl]methoxybenzoate (2.00 g) and sodium methoxide (63 mg) are dissolved in absolute methanol (20 ml) and thereto is added cyclohexene oxide (5.34 ml) in 6 portions (i.e. 0.89 ml×6 times) over a period of 3 days under refluxing. The reaction mixture is concentrated under reduced pressure and the residue is washed with n-hexane three times. After salting out, the residue is extracted with ethyl acetate (about 100 ml). The extract is dried over anhydrous magnesium sulfate and concentrated under reduced pressure to give the oily product (methyl ester compound).

This product is dissolved in about 20% aqueous methanol (75 ml) without isolation and sodium hydroxide (0.40 g) is added thereto. The mixture is heated with stirring at 60° C. for 18 hours, concentrated under reduced pressure and to the residue are added water and 1N hydrochloric acid (10 ml). The precipitated crystal is collected by filtration and recrystallized from about 20% aqueous methanol to give the desired product (2.24 g), m.p. 203°–208° C.

NMR (DMSO-d6) δ ppm: 7.89 (d, 2H, J=8.6 Hz), 7.51 (d, 2H, J=9.0 Hz), 7.08–6.90 (m, 4H), 4.95–4.66 (m, 1H), 4.16–3.40 (m, 6H), 3.10–2.21 (m, 3H), 2.13–1.01 (m, 8H).

EXAMPLE 87

4-[1-[4-(2-Hydroxycyclopentyloxy)phenyl]-2-pyrrolidon-4-yl]methoxybenzoic acid is obtained in the same manner as in Example 86, m.p. 176°–178° C.

EXAMPLES 88 AND 89

Using the suitable starting materials, the compounds of the following Examples 88 and 89 are obtained in the same manner as in Example 85.

EXAMPLE 88

(1) Methyl 4-[1-[4-(1-hydroxycyclohexan-1-yl)methoxyphenyl]-2-pyrrolidon-4-yl]methoxybenzoate, m.p. 138°–141° C.

(2) 4-[1-[4-(1-Hydroxycyclohexan-1-yl)methoxyphenyl]-2-pyrrolidon-4-yl]methoxybenzoic acid, m.p. 190.5°–193° C.

EXAMPLE 89

(1) Methyl 4-[1-[4-(1-hydroxycyclopentan-1-yl)methoxyphenyl]-2-pyrrolidon-4-yl]methoxybenzoate, m.p. 128°–130° C.

(2) 4-[1-[4-(1-Hydroxycyclopentan-1-yl)methoxyphenyl]-2-pyrrolidon-4-yl]methoxybenzoic acid, m.p. 185°–187° C.

Using the suitable starting materials, the compounds of the following Example 90 are obtained in the same manner as in Example 75.

EXAMPLE 90

(1) Methyl 4-[1-[4-(3,4,5-trimethoxybenzyloxy)phenyl]-2-pyrrolidon-4-yl]methoxybenzoate NMR (CDCl3) δ ppm: 7.99 (d, 2H, J=8.1 Hz), 7.51 (d, 2H, J=8.8 Hz), 6.98 (d, 2H, J=8.8 Hz), 6.91 (d, 2H, J=8.1 Hz), 6.64 (s, 2H), 4.97 (s, 2H), 4.25–3.58 (m, 16H), 3.15–2.40 (m, 3H).

(2) 4-[1-[4-(3,4,5-Trimethoxybenzyloxy)phenyl]-2-pyrrolidon-4-yl]methoxybenzoic acid, m.p. 145°–147° C.

This invention is illustrated by the following preparations and the pharmacological test, wherein the derivatives of this invention are used.

| Preparation 1 | |
|---|---|
| Compound of Example 2 | 200 mg |
| Glucose | 250 mg |
| Water for injection | q.s. |
| Total | 5 ml |

After the compound of Example 2 and glucose are dissolved in water for injection, the solution is poured into a 5 ml ampoule, and after purging with nitrogen, sterilized under pressure at 121° C. for 15 minutes to give an injection preparation having the above composition.

| Preparation 2 | |
|---|---|
| Compound of Example 3 | 100 g |
| Abicel (trade name, manufactured by Asahi Chemical Industry, Co., Ltd.) | 40 g |
| Corn starch | 30 g |
| Magnesium stearate | 2 g |
| TC-5 (trade name of hydroxypropyl methyl cellulose, manufactured by Shin-Etsu Chemical Co., Ltd.) | 10 g |
| Polyethlene glycol-6000 | 3 g |
| Castor oil | 40 g |
| Ethanol | 40 g |

The compound of Example 3, Abicel, corn starch and magnesium stearate are mixed and kneaded, and the mixture is tabletted with a pounder (R 10 mm) for sugar coating. The resulting tablets are film-coated with a film coating agent consisting of TC-5, polyethylene glycol-6000, castor oil and ethanol to give a film-coated preparation having the abovementioned composition.

| Preparation 3 | |
|---|---|
| Compound of Example 4 | 2 g |
| Purified lanolin | 5 g |
| Bleached beeswax | 5 g |
| White vaseline | 88 g |
| Total | 100 g |

Bleached beeswax is heated until it becomes liquid, and thereto are added the compound of Example 4, purified lanolin and white vaseline. The mixture is heated until it becomes liquid, and then, stirred until it starts to solidify to give an ointment having the abovementioned composition.

Pharmacological Test

Test of effect on biosynthesis system of sterol or fatty acid by using rat liver slices:

In this test, male Wistar rats (weight; about 200 g) are killed and their livers are taken out and perfused with cold Krebs-Ringer bicarbonate buffer solution (hereinafter referred to KRB), and cut into small slices. Using the small liver slices, the test is carried out in the following manner referring to the following literature.

Bortz, W. M. and Steele, L. A. (1973), Biochim. Biophys. Acta, 306, 85–94

Tsujita, Y., Kuroda, M., Shimada, Y., Tanzawa, K., Arai, M., Kaneko, I., Tanaka, M., Masuda, H., Tarumi, C., Watanabe, Y. and Fujii, S. (1986), Biochim. Biophys. Acta, 877, 50–60

That is to say, the above-mentioned small liver slices (100 mg) are weighed and added into the KRB (1 ml) containing [1-$^{14}$C] acetic acid (2 $\mu$Ci/2 $\mu$mol) and a prescribed amount of test compounds, and the mixture is reacted with shaking at 37° C. for 2 hours under atmosphere of 95% $O_2$/5% $CO_2$. Thereafter, to the reaction mixture is added 15% solution of sodium hydroxide in ethanol (1 ml), and the mixture is further heated at 75° C. for 2 hours. After cooling, petroleum ether (2 ml) is added to the mixture, and it is shaken and separated into layers. The petroleum ether layer (upper layer) is extracted. The petroleum ether layer is concentrated to dryness, and thereto digitonin solution (1 ml) is added and sterol is collected in the resulting precipitation fraction. This fraction is washed with diethyl ether and dissolved in acetic acid (1 ml), and the radioactivity of the sample is measured to determine the sterol biosynthesis activity.

On the basis of the value obtained in the control test, in which the above procedure is repeated except that no test compound is used, the concentration ($\mu$M) of the test compound inhibiting 50% of sterol biosynthesis activity is calculated, which is shown as 50% inhibitory concentration.

On the other hand, hydrochloric acid is added into the lower layer obtained by extraction with petroleum ether in the above procedure, and the mixture is extracted with petroleum ether under an acidic condition, and the extract is concentrated, and then, the radioactivity is measured likewise to determine the fatty acid biosynthesis activity. Likewise as above, on the basis of the fatty acid biosynthesis activity obtained in the control test, 50% fatty acid biosynthesis activity inhibitory concentration of the test compounds is determined.

The obtained results are shown in the following Table 1.

TABLE 1

| Test sample | 50% Inhibitory conc. ($\mu$M) | |
| (Ex. No.) | Sterol | Fatty acid |
| --- | --- | --- |
| 1 (5) | 7.9 | 6.7 |
| 2 (5) | 9.5 | 8.0 |
| 3 (5) | 7.5 | 6.2 |
| 6 (5) | 19.1 | 8.2 |
| 7 (5) | 7.8 | 4.2 |
| 8 (5) | 7.5 | 5.9 |
| 9 (5) | 13.9 | 6.8 |
| 12 (5) | 18.9 | 8.8 |
| 13 (5) | 34.2 | 17.9 |
| 14 (5) | 8.3 | 4.2 |
| 15 (5) | 14.2 | 7.9 |
| 17 (5) | 10.5 | 7.7 |
| 25 (4) | 15.5 | 7.6 |
| 29 (4) | 31.1 | 7.3 |
| 32 (4) | 16.2 | 8.7 |
| 36 (2) | 6.6 | 5.2 |
| 43 (4) | 23.0 | 8.9 |
| 52 (3) | 8.6 | 6.7 |
| 56 (3) | 9.6 | 6.0 |

TABLE 1-continued

| Test sample | 50% Inhibitory conc. ($\mu$M) | |
| (Ex. No.) | Sterol | Fatty acid |
| --- | --- | --- |
| 57 (2) | 20.16 | 10.34 |
| 62 (2) | 13.59 | 6.60 |
| 68 (5) | >50 | 19.15 |
| 70 (2) | 27.23 | 18.44 |
| 71 (4) | 14.83 | 5.81 |
| 72 (4) | 15.25 | 6.21 |
| 74 (2) | 10.56 | 7.08 |
| 76 (2) | 23.36 | 7.60 |
| 79 (2) | 13.35 | 7.66 |
| 80 (2) | 13.06 | 7.02 |
| 84 (2) | 15.92 | 6.47 |
| 88 (2) | 28.43 | 12.93 |
| 90 (2) | 18.42 | 10.45 |

We claim:

1. A compound having the following formula:

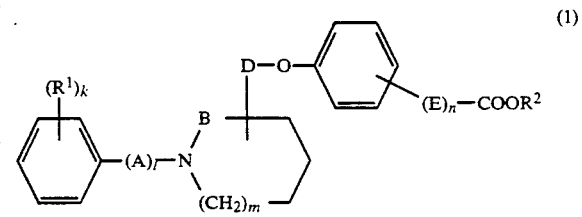

(1)

wherein
R$^1$ is a halogen atom, a $C_1$–$C_6$ alkyl group, a $C_3$–$C_8$ cycloalkyl group, a hydroxy group, a $C_1$–$C_6$ alkoxy group, a phenoxy group which has a substituent selected from a halogen atom and a $C_1$–$C_6$ alkyl group, a carboxyl group, a $c_1$–$C_6$ alkylsulfonyloxy group, a phenylsulfonyloxy group which may optionally be substituted by a halogen atom, a $C_1$–$C_6$ alkylsulfonyloxy($C_1$–$C_6$) alkoxy group, an amino group, a $C_2$–$C_6$ alkanoylamino group, a benzoylamino group, a $C_2$–$C_6$ alkenyloxy group, a phenyl($C_1$–$C_6$)alkoxy($C_1$–$C_6$)alkoxy group, a hydroxy-substituted $C_1$–$C_6$ alkoxy group, a phenyl(-$C_1$–$C_6$)alkoxy group which may optionally have one to three substituents selected from a halogen atom, a $C_1$–$C_6$ alkyl group and a $C_1$–$C_6$ alkoxy group on the phenyl ring, a halogen-substituted $C_1$–$C_6$ alkyl group, a $C_3$–$C_8$ cycloalkyloxy group which may optionally be substituted by a hydroxy group, a $C_1$–$C_6$ alkoxy group substituted by a $C_3$–$C_8$ cycloalkyl group having optionally a hydroxy substituent, an imidazolyl($C_1$–$C_6$) alkyl group, or an imidazolyl($C_1$–$C_6$)alkoxy group; k is 0 or an integer of 1 to 3; or (R$^1$)$_k$ may be a $C_1$–$C_4$ alkylenedioxy group;
A is a $C_1$–$C_6$ alkylene group or a $C_1$–$C_6$ alkylenoxy group; is 0 or 1;
B is a methylene group or a carbonyl group;
m is 0 or 1;
D is a $C_1$–$C_6$ alkylene group;
E is a $C_1$–6 alkylene group or a $C_2$–$C_6$ alkenylene group;
n is 0 or 1; and
R$^2$ is a hydrogen atom or a $C_1$–$C_6$ alkyl group; or a pharmaceutically acceptable salt thereof.

2. The compound according to claim 1, wherein B is a carbonyl group.

3. The compound according to claim 1, wherein B is a methylene group.

4. The compound according to claim 3, wherein l is 0, is 0 and n is 0.

5. The compound according to claim 2, wherein m is 0.

6. The compound according to claim 2, wherein m is 1.

7. The compound according to claim 6, wherein l is 0 and n is 0.

8. The compound according to claim 5, wherein l is 0.

9. The compound according to claim 5, wherein l is 1 and A is a $C_1$–$C_6$ alkylene group.

10. The compound according to claim 5, wherein l is 1 and A is a $C_1$–$C_6$ alkylenoxy group.

11. The compound according to claim 8, wherein n is 0.

12. The compound according to claim 8, wherein n is 1.

13. The compound according to claim 11, wherein $R^2$ is a hydrogen atom.

14. The compound according to claim 11, wherein $R^2$ is a $C_1$–$C_6$ alkyl group.

15. The compound according to claim 14, wherein k is an integer of 1 to 3, and $R^1$ is a halogen atom or a $C_1$–$C_6$ alkyl group.

16. The compound according to claim 13, wherein k is an integer of 1 to 3 and $R^1$ is a $C_1$–$C_6$ alkyl group.

17. The compound according to claim 16, wherein k is 1 and D is a methylene group.

18. The compound according to claim 13, wherein k is an integer of 1 to 3 and $R^1$ is a halogen atom.

19. The compound according to claim 18, wherein k is 1 and D is a methylene group.

20. The compound according to claim 13, wherein k is an integer of 1 to 3 and $R^1$ is a $C_1$–$C_6$ alkoxy group, a $C_2$–$C_6$ alkenyloxy group, a hydroxy-substituted $C_1$–$C_6$ alkoxy group, a phenyl($C_1$–$C_6$)alkoxy group which may optionally have one to three substituents selected from a halogen atom, a $C_1$–$C_6$ alkyl group and a $C_1$–$C_6$ alkoxy group on the phenyl ring, or a $C_3$–$C_8$ cycloalkyloxy group which may optionally be substituted by a hydroxy group.

21. The compound according to claim 13, wherein k is an integer of 1 to 3, and $R^1$ is a halogen atom, a $C_1$–$C_6$ alkyl group, a $C_3$–$C_8$ cycloalkyl group, a hydroxy group, a phenoxy group which has a substituent selected from a halogen atom and a $C_1$–$C_6$ alkyl group, a carboxyl group, a $C_1$–$C_6$ alkylsulfonyloxy group, a phenylsulfonyloxy group which may optionally be substituted by a halogen atom, a $C_1$–$C_6$ alkylsulfonyloxy($C_1$–$C_6$)alkoxy group, an amino group, a $C_2$–$C_6$ alkanoylamino group, a benzoylamino group, a phenyl($C_1$–$C_6$)alkoxy($C_1$–$C_6$)alkoxy group, a halogen-substituted $C_1$–$C_6$ alkyl group, a $C_1$–$C_6$ alkoxy group substituted by a $C_3$–$C_8$ cycloalkyl group having optionally a hydroxy substituent, an imidazolyl($C_1$–$C_6$)alkyl group, or an imidazolyl($C_1$–$C_6$)alkoxy group.

22. The compound according to claim 1 which is selected from the following compounds:
4[1-(4-tert-butylphenyl)-2-pyrrolidon-4-yl]methoxybenzoic acid,
4[1-(4-chlorophenyl)-2-pyrrolidon-4-yl]methoxybenzoic acid,
4[1-(4-ethoxyphenyl)-2-pyrrolidon-4-yl]methoxybenzoic acid,
4[1-(4-methoxybenzyloxy)phenyl]-2-pyrrolidon-4-yl]methoxybenzoic acid.
4[1-(4-allyloxyphenyl)-2-pyrrolidon-4-yl]methoxybenzoic acid,
4[1-(4-methallyloxyphenyl)-2-pyrrolidon-4-yl]methoxybenzoic acid
4[1-(4-hydroxyethoxy)phenyl]-2-pyrrolidon-4-yl]methoxybenzoic acid, and
4[1-(4-cyclopentyloxyphenyl)-2-pyrrolidon-4-yl]methoxybenzoic acid.

23. A hypolipidemic composition which contains an effective amount of the compound or a pharmaceutically acceptable salt thereof as set forth in claim 1 in admixture with a pharmaceutically acceptable carrier or diluent.

24. A method for the treatment of hyperlipidemia, which comprises administering an effective amount of the compound or a pharmaceutically acceptable salt thereof as set forth in claim 1 to a patient.

* * * * *